United States Patent
Noguchi et al.

(10) Patent No.: US 10,226,233 B2
(45) Date of Patent: Mar. 12, 2019

(54) ULTRASOUND DIAGNOSTIC APPARATUS

(71) Applicant: FUJIFILM Corporation, Tokyo (JP)

(72) Inventors: Masafumi Noguchi, Ashigara-kami-gun (JP); Yukiya Miyachi, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 79 days.

(21) Appl. No.: 14/094,373

(22) Filed: Dec. 2, 2013

(65) Prior Publication Data

US 2014/0088423 A1 Mar. 27, 2014

Related U.S. Application Data

(63) Continuation of application No. PCT/JP2012/063953, filed on May 30, 2012.

(30) Foreign Application Priority Data

Jun. 3, 2011 (JP) .................. 2011-125183

(51) Int. Cl.
  *A61B 8/00* (2006.01)
  *A61B 8/08* (2006.01)
(52) U.S. Cl.
  CPC ............ *A61B 8/485* (2013.01); *A61B 8/0891* (2013.01); *A61B 8/486* (2013.01); *A61B 8/5276* (2013.01); *A61B 8/543* (2013.01)
(58) Field of Classification Search
  USPC ................................................. 382/128–132
  See application file for complete search history.

(56) References Cited

U.S. PATENT DOCUMENTS

| 5,840,028 A | 11/1998 | Chubachi et al. |
| 8,064,983 B2 * | 11/2011 | Salla et al. ................... 600/413 |
| 2002/0072674 A1 * | 6/2002 | Criton et al. ................. 600/454 |
| 2004/0066398 A1 * | 4/2004 | Dolimier ................ A61B 8/463 715/720 |
| 2006/0084871 A1 * | 4/2006 | Akaki ...................... A61B 8/13 600/437 |
| 2006/0241449 A1 * | 10/2006 | Oonuki .......................... 600/443 |
| 2007/0038086 A1 * | 2/2007 | Ohtsuka ........................ 600/437 |
| 2010/0081931 A1 * | 4/2010 | Destrempes et al. ......... 600/437 |

(Continued)

FOREIGN PATENT DOCUMENTS

| JP | 10-5226 A | 1/1998 |
| JP | 2010-233956 A | 10/2010 |

OTHER PUBLICATIONS

Peter R. Hoskins, Kevin Martin, Abigail Thrush, "Diagnostic Ultrasound: Physics and Equipment", Cambridge University Press, Jun 17, 2010.*

(Continued)

*Primary Examiner* — Carolyn Pehlke
(74) *Attorney, Agent, or Firm* — Birch, Stewart, Kolasch & Birch, LLP

(57) ABSTRACT

Provided is an ultrasound diagnostic apparatus that measures the modulus of elasticity of a vascular wall, wherein only M-mode images for heartbeats necessary for the measurement are displayed. The problem is solved by, when freeze is implemented during a B/M-mode display, displaying an M-mode image after discarding a heartbeat at the time of freeze and possibly also a heartbeat immediately before freeze.

11 Claims, 14 Drawing Sheets

(56) References Cited

U.S. PATENT DOCUMENTS

2010/0113930 A1    5/2010  Miyachi
2010/0210948 A1*   8/2010  Nishimura .................... 600/454
2011/0046485 A1*   2/2011  Nakata ......................... 600/440

OTHER PUBLICATIONS

Laskowski (Mayo Clinic, https://www.mayoclinic.org/healthy-lifestyle/fitness/expert-answers/heart-rate/faq-20057979, Aug. 22, 2015).*
Merriam-Webster entry for "corresponding" (https://www.merriam-webster.com/dictionary/corresponding?utm_campaign=sd&utm_medium=serp&utm_source=jsonId, updated Dec. 19, 2017.*
Extended European Search Report dated Oct. 21, 2014 issued in European Patent Application No. 12793462.8.
International Preliminary Report on Patentability dated Dec. 19, 2013, issued in PCT/JP2012/063953 (Forms PCT/IB/338; PCT/IB/373 and PCT/IB/237).
International Search Report, dated Jun. 26, 2012, issued in PCT/JP2012/063953.

* cited by examiner

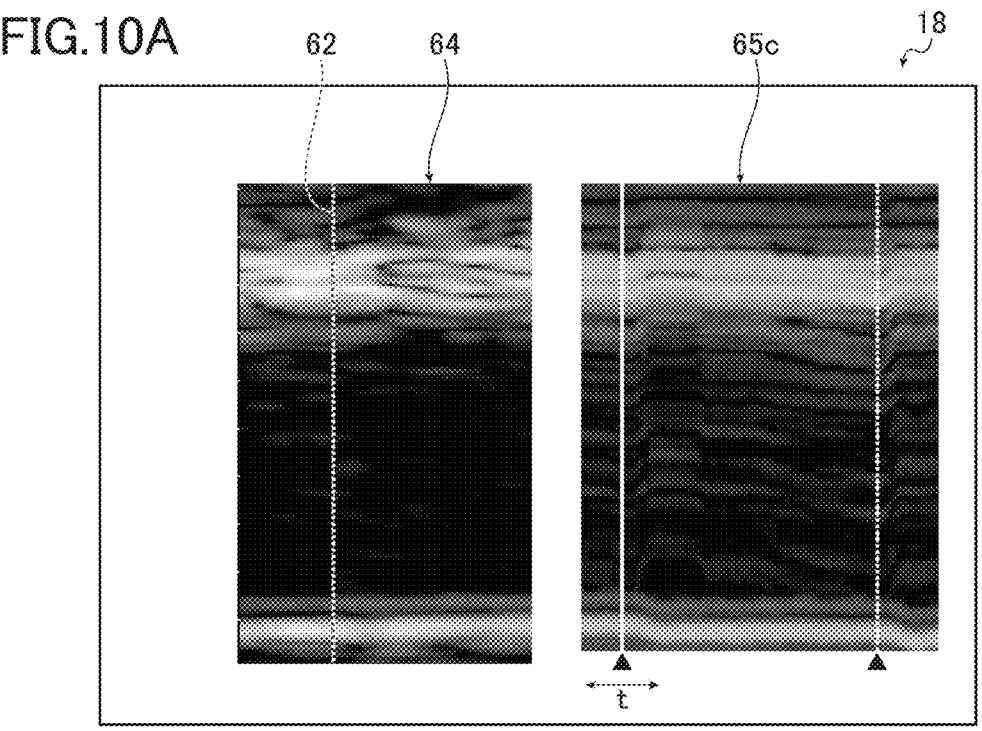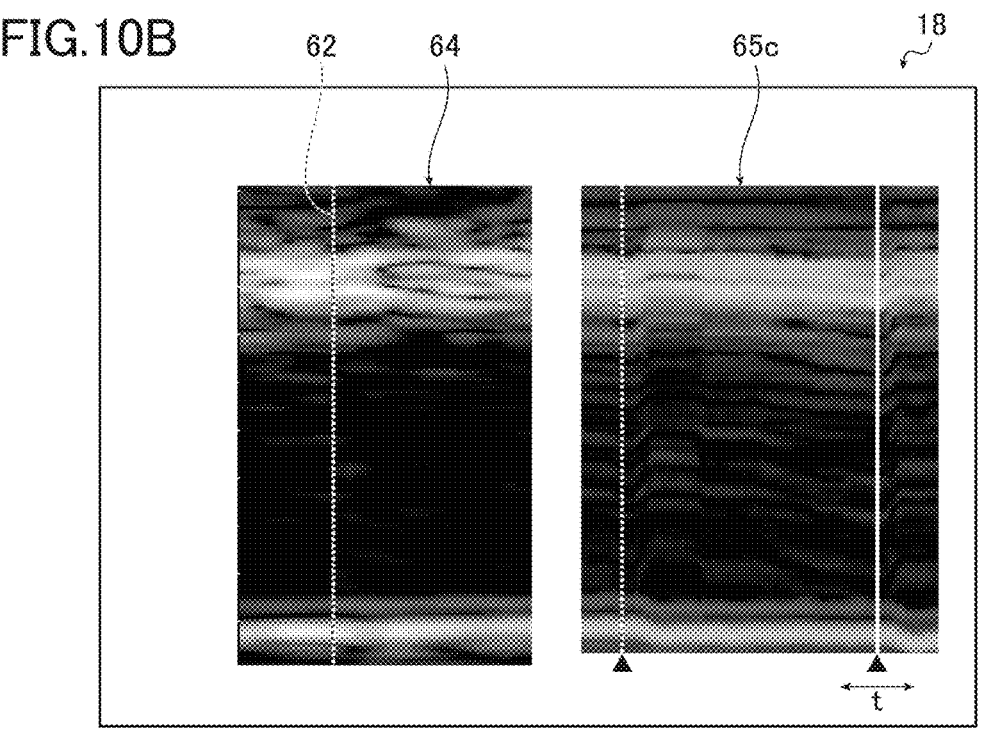

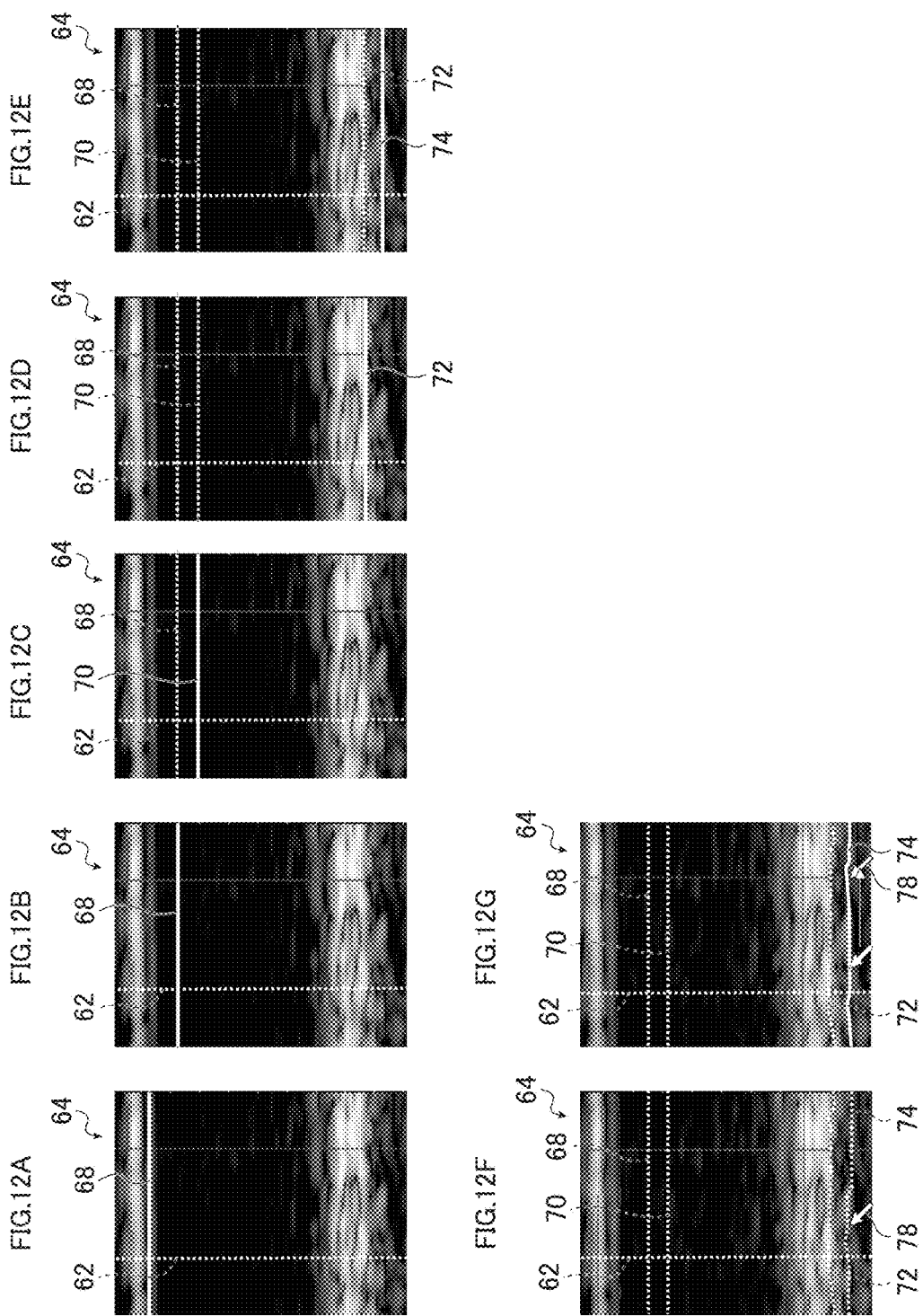

ULTRASOUND DIAGNOSTIC APPARATUS

CROSS REFERENCE TO RELATED APPLICATIONS

This application is a Continuation of PCT International Application No. PCT/JP2012/063953 filed on May 30, 2012, which claims priority under 35 U.S.C 119(a) to Application No. 2011-125183 filed in Japan on Jun. 3, 2011, all of which are here by expressly incorporated by reference into the present application.

BACKGROUND OF THE INVENTION

The present invention relates to an ultrasound diagnostic apparatus suitable for measuring an elastic modulus of a vascular wall. In particular, the present invention relates to an ultrasound diagnostic apparatus capable of displaying an M-mode image of a heartbeat suitable for measuring an elastic modulus of a vascular wall in good condition.

Ultrasound diagnostic apparatuses using ultrasound images are put to practical use in the medical field.

In general, this type of ultrasound diagnostic apparatus has an ultrasound probe (hereinafter referred to as a probe) and a diagnostic apparatus body. The ultrasound diagnostic apparatus transmits ultrasonic waves from the probe into a subject's body, receives an ultrasonic echo from the subject's body with the probe, and electrically processes the resulting reception signals in the diagnostic apparatus body to produce an ultrasound image.

Also, ultrasonic waves are transmitted toward a blood vessel, a cardiac wall, or the like, an ultrasonic echo therefrom is received, a reception signal is analyzed to obtain an amount of displacement of a vascular wall or the like, and based on the displacement amount, the elastic modulus of the vascular wall, the cardiac wall (heart muscle) or the like is measured.

For example, JP 10-5226 A describes that ultrasonic waves are transmitted and received to and from an object moving in synchronization with heartbeats (cardiac pulsation) to obtain a reception signal of an ultrasonic echo, the instantaneous position of the object is determined based on the amplitude and phase of the reception signal, and the large amplitude displacement motion of the vascular wall based on the heartbeats is tracked, thereby obtaining the elastic modulus of the blood vessel.

Specifically, a motion velocity waveform of minute vibration of the vascular wall is obtained based on a sequential position of the vascular wall, a tracking trajectory of each of sections given at predetermined intervals in the depth direction in the vascular wall is obtained, and a temporal change in thickness of each section is calculated to obtain the elastic modulus of the blood vessel.

JP 2010-233956 A also describes an ultrasound diagnostic apparatus which obtains an amount of displacement of a blood vessel or the like from a reception signal of an ultrasonic echo obtained by transmitting and receiving ultrasonic waves to and from an object moving in synchronization with heartbeats, and obtains an elastic modulus from the displacement amount.

In this ultrasound diagnostic apparatus, a B-mode image and an M-mode image are produced using a reception signal obtained from an object such as a blood vessel, blurring due to hand or body movement is detected from the reception signal of the M-mode image, a positional variation of the probe and the subject is detected using the reception signal of the M-mode image where the blurring is detected, the accuracy of the reception signal is determined from the detection result, an amount of displacement of the object is obtained using the reception signal of the M-mode image whose accuracy is determined to be high, and the elastic modulus of the vascular wall or the like is measured from the displacement amount.

In order to accurately measure an elastic modulus of a blood vessel or the like based on such a displacement amount of an object moving in synchronization with heartbeats, the analysis needs to be performed particularly with an M-mode image which has a heartbeat suitable for analysis and is less affected by blurring due to hand movement of the tester or body movement of the subject, irregular heartbeats, speckles (speckle noise or speckle pattern) or the like.

Accordingly, for instance, the ultrasound diagnostic apparatus stated in JP 2010-233956 A detects blurring due to hand movement of the tester or body movement of the subject and measures the elastic modulus from the displacement amount of the vascular wall or the like using the reception signal of the heartbeat which is not affected by the blurring due to hand movement and has high accuracy.

Here, in order to measure an accurate elastic modulus of a vascular wall, the analysis needs to be performed using an M-mode image of a complete heartbeat which is fully included from the start through the end (which is fully captured), in addition to being not affected by blurring due to hand movement or the like.

SUMMARY OF THE INVENTION

In a conventional ultrasound diagnostic apparatus, when freeze (pausing of an image) is performed to analyze the image, the image at the time the freeze is performed is displayed as the M-mode image to be subjected to the analysis.

Accordingly, in some cases, the displayed M-mode image may not have a complete heartbeat suitable for analysis to be carried out to measure an elastic modulus of a vascular wall. When a plurality of heartbeats are displayed, even though a complete heartbeat exists, the image displaying the heartbeat is to be small, resulting in the decrease in visibility.

In the ultrasound diagnostic apparatus, freeze is generally performed by depressing a freeze button provided on an operating panel.

At the time when such operation as depression of a button is performed, blurring due to hand movement easily occurs. Accordingly, even though one or more complete heartbeats exist in an M-mode image, a displayed image does not necessarily include a heartbeat suitable for analysis.

An object of the invention is to solve the problems of the prior art and to provide an ultrasound diagnostic apparatus which can efficiently display an M-mode image having a heartbeat suitable for the measurement of an elastic modulus of a vascular wall under the condition where the image is frozen.

In order to attain the foregoing object, an ultrasound diagnostic apparatus comprises an ultrasound probe which has ultrasound transducers transmitting ultrasonic waves, receiving an ultrasonic echo reflected by a subject, and outputting a reception signal according to the received ultrasonic echo; an image producing unit adapted to produce a B-mode image and an M-mode image from the reception signal output from the ultrasound transducers; a display; a display processing unit adapted to display at least one of the B-mode image and the M-mode image produced by the image producing unit on the display; a freeze instructing unit adapted to instruct pausing of an image; and a heartbeat detecting unit adapted to detect a heartbeat in the M-mode image, wherein when image pausing is instructed by the freeze instructing unit under a condition where the B-mode image and the M-mode image are displayed on the display, the display processing unit displays on the display an M-mode image produced by the image producing unit after discarding at least a part of a heartbeat which is detected by the heartbeat detecting unit and is corresponding to a time point when the image pausing is instructed from the M-mode image.

Preferably, in the ultrasound diagnostic apparatus as described above, when image pausing is instructed by the freeze instructing unit, the display processing unit displays the M-mode image and the B-mode image as arranged in a longitudinal direction of the display.

Preferably, the M-mode image and the B-mode image are same in magnification.

Preferably, when image pausing is instructed by the freeze instructing unit, the display processing unit displays on the display an M-mode image after discarding a whole of the heartbeat which is detected by the heartbeat detecting unit and is corresponding to the time point when the image pausing is instructed and also discarding at least a part of a heartbeat which is detected by the heartbeat detecting unit and is of immediately before the time point when the image pausing is instructed by the freeze instructing unit.

Preferably, as display modes of an image to be displayed on the display by the display processing unit when image pausing is instructed by the freeze instructing unit, a first display mode that displays an M-mode image after discarding at least a part of the heartbeat which is detected by the heartbeat detecting unit and is corresponding to the time point when the image pausing is instructed, and a second display mode that displays an M-mode image after discarding a whole of the heartbeat which is detected by the heartbeat detecting unit and is corresponding to the time point when the image pausing is instructed and also discarding at least a part of a heartbeat which is detected by the heartbeat detecting unit and is of immediately before the time point when the image pausing is instructed by the freeze instructing unit, are set, and the ultrasound diagnostic apparatus further comprises a mode selection instructing unit adapted to select one of the display modes.

It is preferred to have a vascular wall boundary setting instructing unit adapted to set a boundary position of a vascular wall in the B-mode image after image pausing is instructed by the freeze instructing unit.

Preferably, when image pausing is instructed by the freeze instructing unit, the display processing unit displays on the display a B-mode image corresponding to a start time of a latest heartbeat in the M-mode image displayed on the display.

It is preferred to have a region-of-interest setting instructing unit adapted to set a region of interest in a B-mode image displayed on the display.

Preferably, a frame rate of ultrasonic waves transmitted by the ultrasound transducers is increased in response to an instruction to set the region of interest to be higher than before the instruction to set the region of interest.

The ultrasound diagnostic apparatus of the invention having the foregoing configuration detects a heartbeat in an M-mode image when an image is frozen in so-called B/M mode display and displays the M-mode image after discarding a heartbeat of when the freeze is performed and possibly also a heartbeat immediately before the freeze.

Consequently, according to the ultrasound diagnostic apparatus of the invention, it becomes possible to discard an incomplete heartbeat which is not fully included from the start through the end, and an unnecessary heartbeat such as a heartbeat which is likely to be affected by blurring due to hand movement or the like, thereby displaying an M-mode image having a heartbeat suitable for analysis with good visibility.

In particular, when a B-mode image and an M-mode image are laterally arranged, the M-mode image having a heartbeat which is considered as suitable for analysis can be enlarged and arranged beside the B-mode image. Consequently, the tester can perform processes and determination while viewing the large B-mode image and the large M-mode image.

Therefore, according to the invention, the tester such as a doctor who operates the ultrasound diagnostic apparatus can perform processes such as inputting an instruction, determination, and the like while observing an M-mode image which has a heartbeat suitable for analysis and has good visibility, thereby enabling to stably perform accurate measurement of an elastic modulus of a vascular wall or the like.

BRIEF DESCRIPTION OF THE DRAWINGS

FIGS. 10A and 10B are conceptual diagrams each showing an example of image display in the ultrasound diagnostic apparatus shown in FIG. 1.

FIGS. 12A to 12G are conceptual diagrams each showing an example of image display in the ultrasound diagnostic apparatus shown in FIG. 1.

DETAILED DESCRIPTION OF THE INVENTION

An ultrasound diagnostic apparatus of the invention is described in detail below with reference to the preferred embodiments shown in the accompanying drawings.

Figure 1:
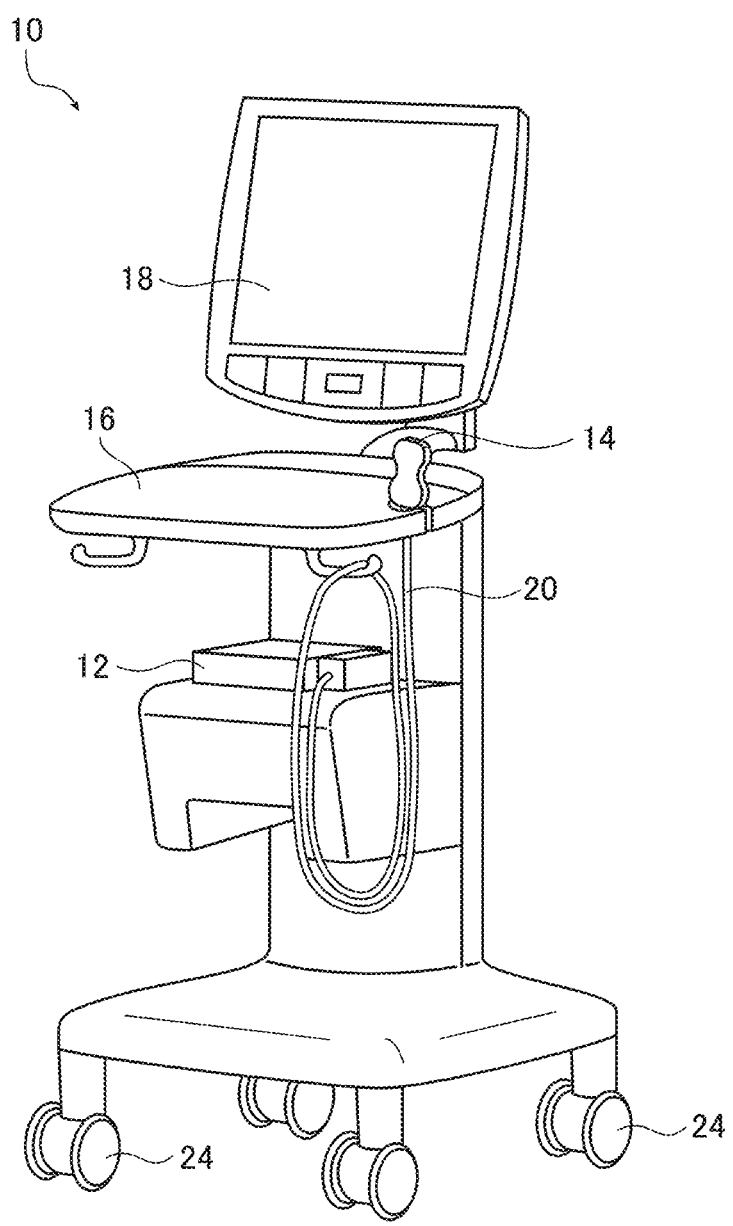
FIG. 1 is a conceptual diagram showing an example of an ultrasound diagnostic apparatus of the invention.

FIG. 1 conceptually shows the appearance of an example of the ultrasound diagnostic apparatus of the invention.

As shown in FIG. 1, an ultrasound diagnostic apparatus 10 basically has a diagnostic apparatus body 12, an ultrasound probe 14, an operating panel 16, and a display 18. Casters 24 are arranged at the bottom of the ultrasound diagnostic apparatus 10 so that the apparatus can be easily moved by human power.

The ultrasound probe 14 (hereinafter referred to as a probe 14) performs transmission and reception of ultrasonic waves, and supplies a reception signal according to a received ultrasonic echo to the diagnostic apparatus body 12.

The probe 14, which is a known ultrasound probe used in various ultrasound diagnostic apparatuses, has so-called ultrasound transducers (ultrasonic piezoelectric elements) arranged in a one-dimensional or two-dimensional array which transmit ultrasonic waves toward a subject, receive an ultrasonic echo reflected by the subject, and output an electrical signal (reception signal) according to the received ultrasonic echo.

In the invention, the type of the probe 14 is not particularly limited, and various types such as a convex type, a linear type and a sector type may be used. An external probe or a radial scan type probe for use in an ultrasound endoscope may be used. In addition, the probe 14 may have an ultrasound vibrator compatible with harmonic imaging for use in receiving second or higher order harmonics of transmitted ultrasonic waves.

In the illustrated example, the probe 14 and the diagnostic apparatus body 12 are interconnected by a cable 20. However, the invention is not limited thereto. A transmission circuit 28, a reception circuit 30, a transmission/reception control unit 32, and the like described below may be arranged in the probe 14, and the probe 14 and the diagnostic apparatus body 12 may be interconnected by wireless communication.

The display 18 is a known display (display device).

In the ultrasound diagnostic apparatus 10, as in various ultrasound diagnostic apparatuses, the display 18 displays an ultrasound image according to a reception signal output from the probe 14, information of the subject, selecting means and instructing means for operation through a GUI (Graphical User Interface), a region of interest (hereinafter abbreviated as ROI), an elasticity measurement result of a vascular wall to be described below, and the like.

The operating panel 16 is provided to operate the ultrasound diagnostic apparatus 10.

Although not illustrated, in the ultrasound diagnostic apparatus 10, the operating panel 16 has arranged therein selecting means for selecting various modes such as a B mode and an M mode, a trackball (track pad/touch pad) for moving a cursor, a line, or the like displayed on the display 18, a set button for determining (confirming) selection or operation, a freeze button for switching between motion image display and still image display, changing means for changing a depth of field of an ultrasound image, gain adjusting means, a zoom button for enlarging an ultrasound image, and the like.

In the ultrasound diagnostic apparatus 10, as the modes, in addition to modes of a common ultrasound diagnostic apparatus such as a B mode and an M mode, a VE mode (Vascular Elasticity mode) for measuring an elastic modulus of a vascular wall is also set.

Figure 7A:
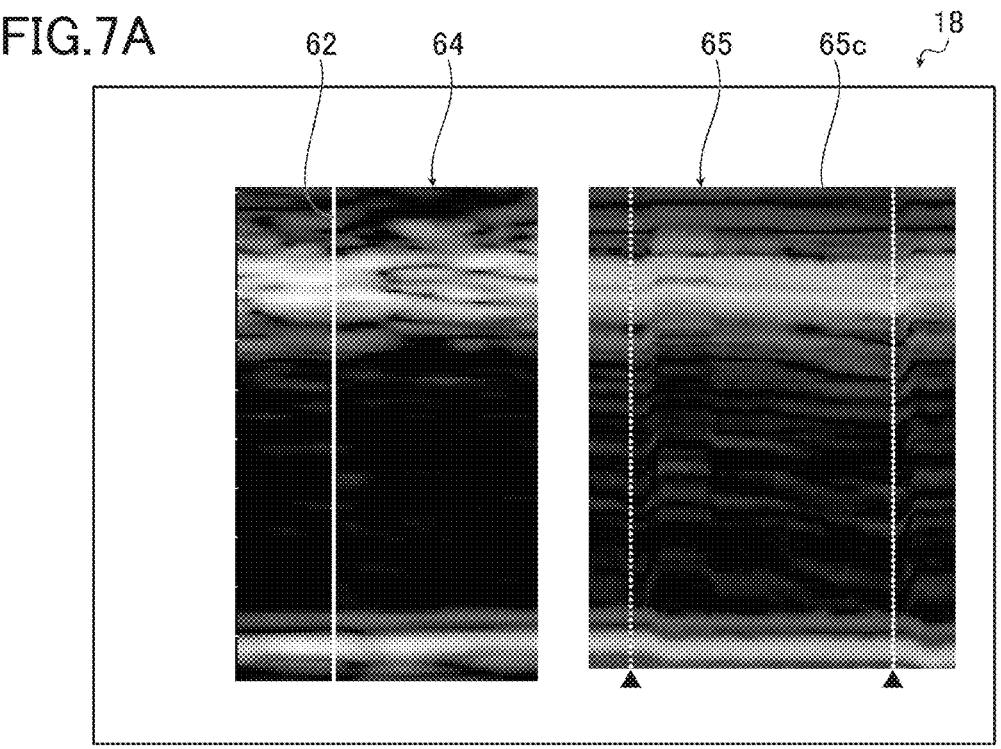
FIGS. 7A and 7B are conceptual diagrams each showing an example of image display in the ultrasound diagnostic apparatus shown in FIG. 1.
Figure 7B:
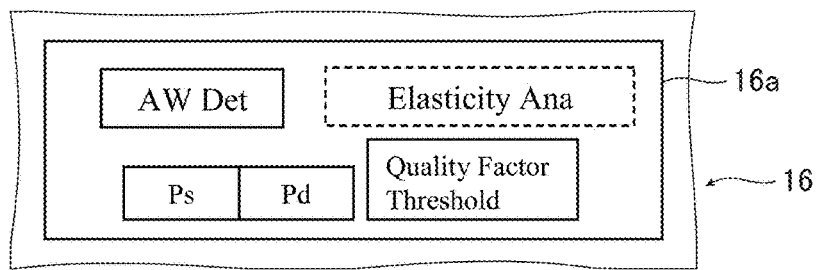

Although not illustrated again, the operating panel 16 also has arranged therein a touch panel 16a which is a display device for operation through the GUI (see FIG. 7B).

The diagnostic apparatus body 12 controls the overall operation of the ultrasound diagnostic apparatus 10 and produces an ultrasound image according to a reception signal output from the probe 14 to be displayed on the display 18, as well as performing various processes for measuring a blood vessel elastic modulus. The diagnostic apparatus body 12 is constituted using, for example, a computer or the like.

Figure 2:
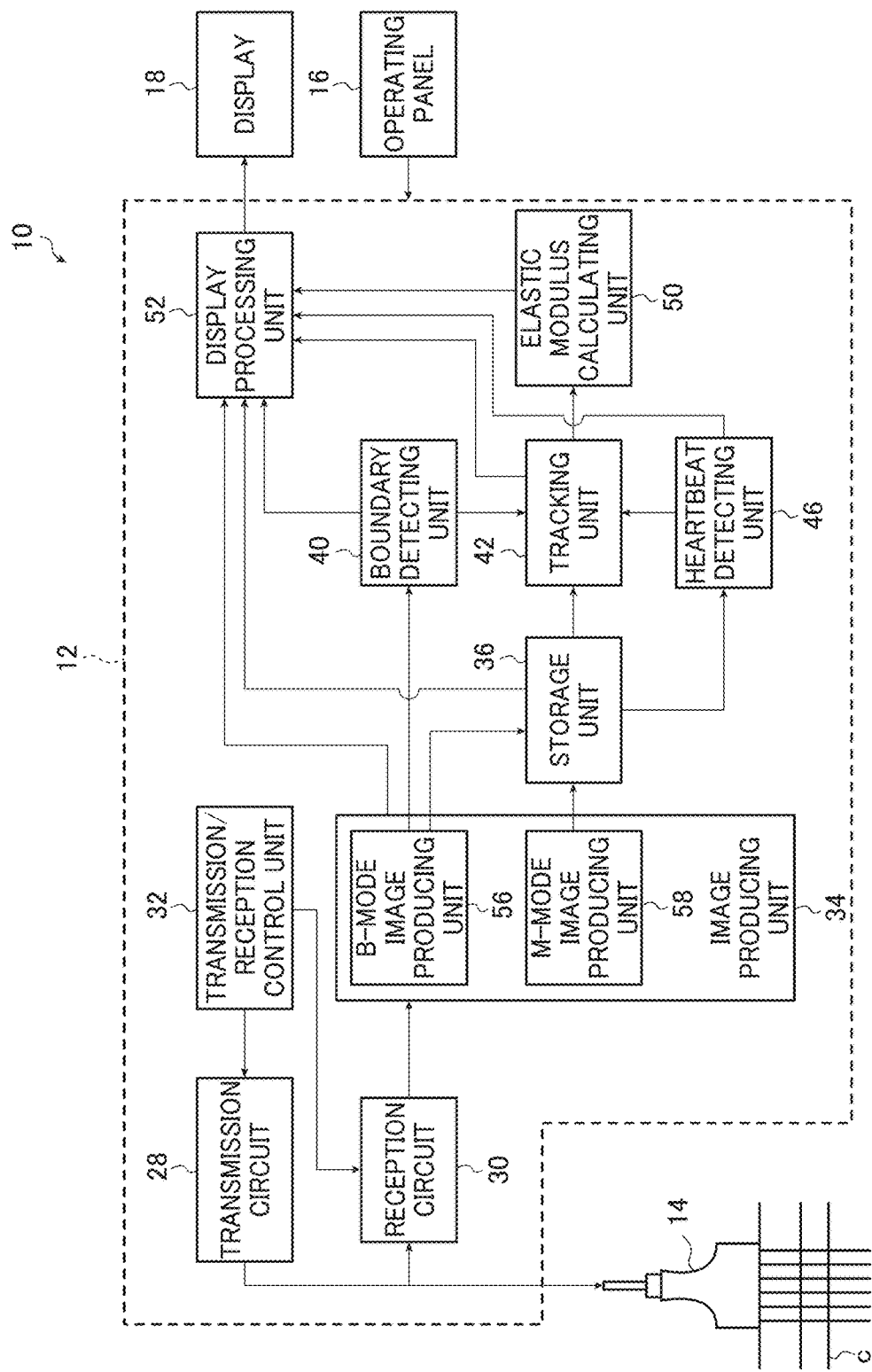
FIG. 2 is a block diagram conceptually showing the configuration of the ultrasound diagnostic apparatus shown in FIG. 1.
Figure 3:
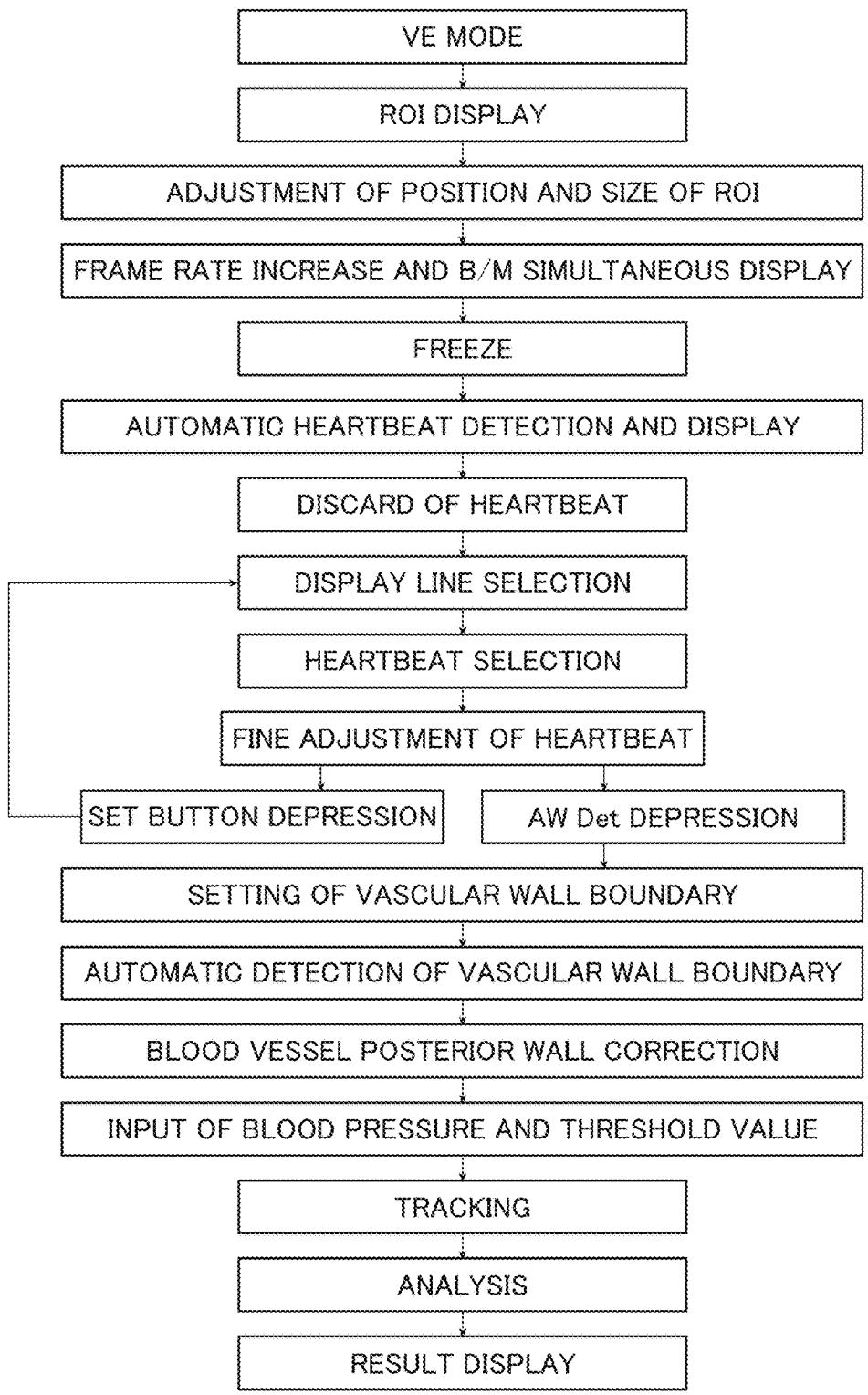
FIG. 3 is a flowchart for explaining an example of elasticity measurement of a vascular wall in the ultrasound diagnostic apparatus shown in FIG. 1.

FIG. 2 is a block diagram conceptually showing the configuration of the ultrasound diagnostic apparatus 10.

As shown in FIG. 2, the diagnostic apparatus body 12 has the transmission circuit 28, the reception circuit 30, the transmission/reception control unit 32, an image producing unit 34, a storage unit 36, a boundary detecting unit 40, a tracking unit 42, a heartbeat detecting unit 46, an elastic modulus calculating unit 50, and a display processing unit 52.

The image producing unit 34 has a B-mode image producing unit 56 and an M-mode image producing unit 58.

The above-mentioned probe 14 is connected to the transmission circuit 28 and the reception circuit 30. The transmission/reception control unit 32 is connected to the transmission circuit 28 and the reception circuit 30. The reception circuit 30 is connected to the image producing unit 34.

The image producing unit 34 is connected to the display processing unit 52. The B-mode image producing unit 56 and the M-mode image producing unit 58 of the image producing unit 34 are connected to the storage unit 36. The B-mode image producing unit 56 is also connected to the boundary detecting unit 40.

The storage unit 36 is connected to the tracking unit 42, the heartbeat detecting unit 46, and the display processing unit 52. The heartbeat detecting unit 46 and the boundary detecting unit 40 are connected to the tracking unit 42 and the display processing unit 52. The tracking unit 42 is connected to the elastic modulus calculating unit 50 and the display processing unit 52. The elastic modulus calculating unit 50 is connected to the display processing unit 52.

The transmission/reception control unit 32 sequentially sets a transmission direction of an ultrasonic beam and a reception direction of an ultrasonic echo of the probe 14 through the transmission circuit 28 and the reception circuit 30.

The transmission/reception control unit 32 also has a transmission control function of selecting a transmission delay pattern in accordance with the set transmission direction and a reception control function of selecting a reception delay pattern in accordance with the set reception direction.

The transmission delay pattern is a pattern of a delay time which is given to a driving signal for each of the ultrasound transducers so as to produce an ultrasonic beam in a desired direction by using ultrasonic waves transmitted from the ultrasound transducers of the probe 14. The reception delay pattern is a pattern of a delay time which is given to a reception signal so as to extract an ultrasonic echo from a desired direction by using ultrasonic waves received by the ultrasound transducers.

A plurality of transmission delay patterns and a plurality of reception delay patterns are stored in an internal memory (not illustrated), and are appropriately selected and used depending on the situation.

The transmission circuit 28 has a plurality of channels and produces a plurality of driving signals to be separately applied to each of the ultrasound transducers of the probe 14. At this time, a delay time can be given to each of the driving signals based on the transmission delay pattern selected by the transmission/reception control unit 32.

The transmission circuit 28 may adjust delay amounts of the driving signals and then supply the adjusted driving signals to the respective ultrasound transducers of the probe 14 so that the ultrasonic waves transmitted from the ultrasound transducers form an ultrasonic beam, or may supply to the probe 14 the driving signals configured so that ultrasonic waves transmitted from the ultrasound transducers at a time reach the entire imaging region of the subject.

The reception circuit 30 which has a plurality of channels similarly to the transmission circuit 28 amplifies a plurality of analog signals received through the ultrasound transducers and converts the amplified analog signals to digital reception signals.

Furthermore, a reception focusing process is performed by giving the delay time to each of the reception signals based on the reception delay pattern selected by the transmission/reception control unit 32 and adding those reception signals. With this reception focusing process, the ultrasonic echo is well focused so as to produce a sound ray signal (sound ray data).

The produced sound ray data is supplied to the image producing unit 34.

The image producing unit 34 performs a preprocess such as Log (logarithmic) compression and gain adjustment on the supplied sound ray data to produce image data of an ultrasound image. Further, the image producing unit 34 converts (raster-converts) the produced image data to image data according to a normal television signal scan system, performs necessary image processes such as a gradation process on the image data, and outputs the image data to the display processing unit 52.

The image producing unit 34 has the B-mode image producing unit 56 which produces a B-mode image, and the M-mode image producing unit 58 which produces an M-mode image. The B-mode image and the M-mode image may be produced by a known method.

The display processing unit 52 produces display data for use in display on the display 18 in accordance with image data of the ultrasound image supplied from the image producing unit 34, image data of the ultrasound image read out from the storage unit 36, the operation (input instruction) made through the operating panel 16, measurement results (analysis results) of a vascular wall elastic modulus described below, and the like, and displays them on the display 18.

In the ultrasound diagnostic apparatus 10 of the illustrated example, the storage unit 36, the boundary detecting unit 40, the tracking unit 42, the heartbeat detecting unit 46, and the elastic modulus calculating unit 50 of the diagnostic apparatus body 12 are mainly used in the VE mode in which an elastic modulus of a vascular wall is measured.

Hereinafter, the respective units such as the storage unit 36 and the boundary detecting unit 40, and the ultrasound diagnostic apparatus 10 of the invention will be explained in further detail by explaining the function of the ultrasound diagnostic apparatus 10 in the VE mode with reference to a flowchart of FIG. 3 and FIGS. 5 to 14.

In the following explanation, with regard to the display on the display 18, the display processing unit 52 performs necessary processes such as production of lines, even though not particularly described.

When an ultrasound diagnosis by the ultrasound diagnostic apparatus 10 is started, under the control by the transmission/reception control unit 32, the transmission circuit 28 causes the ultrasound transducers of the probe 14 to transmit ultrasonic waves, and the reception circuit 30 processes a reception signal output from the probe 14 to produce a sound ray signal and outputs the sound ray signal to the image producing unit 34.

Figure 4:
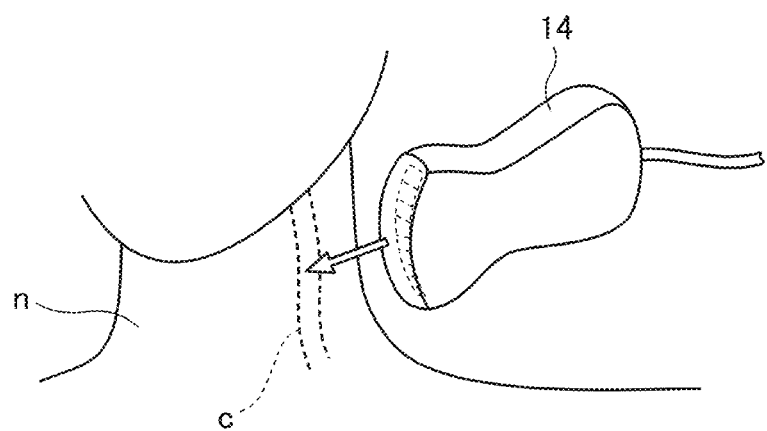
FIG. 4 is a conceptual diagram for explaining an ultrasound diagnosis for elasticity measurement of a vascular wall.

As an example, assuming that the B mode is selected, a carotid artery c of the subject is taken as a measurement target, and the probe 14 is brought into contact with the neck n as conceptually shown in FIG. 4, a B-mode image produced by the image producing unit 34 (B-mode image producing unit 56) is processed by the display processing unit 52 and displayed on the display 18.

Figure 5A:
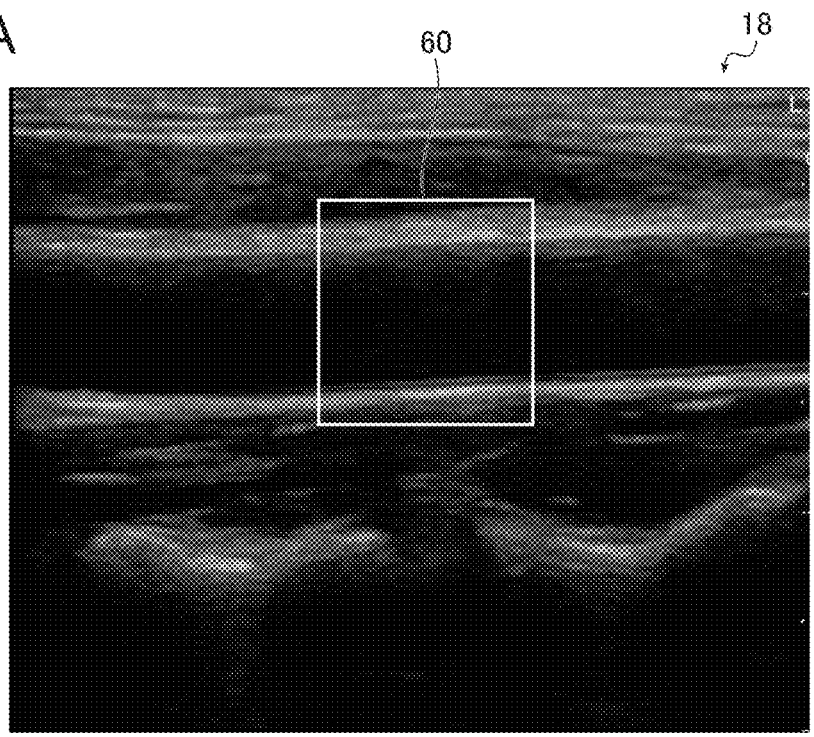
FIGS. 5A and 5B are conceptual diagrams each showing an example of image display in the ultrasound diagnostic apparatus shown in FIG. 1.

When the target carotid artery c can be appropriately observed and the VE mode is selected with the mode selecting means of the operating panel 16 (in the following description, of the operating panel 16" is omitted), the display processing unit 52 displays an ROI 60 representing a region of interest in the B-mode image as conceptually shown in FIG. 5A.

Under this condition, the position of the ROI 60 in the B-mode image can be moved by operation of the trackball. When the set button is pressed, the position of the ROI 60 is fixed and the size of the ROI 60 can be changed by operation of the trackball.

Each time the set button is pressed, the implementable operation is alternately switched between the position change of the ROI 60 and the size adjustment of the ROI 60.

When the zoom button is pressed (depressed) under this condition, it is determined that the adjustment of the position and the size of the ROI 60 has finished and the setting of the ROI 60 has been instructed. In response, the transmission/reception control unit 32 increases the frame rate to be higher than that of before the setting of the ROI 60 is instructed (for example, to be equal to or higher than 200 Hz or at least five times the value of before the ROI setting is instructed). In addition, in response to the depression of the zoom button, the M-mode image producing unit 58 starts to produce an M-mode image of the ROI 60 and, as shown in FIG. 5B, a B-mode image 64 where the portion of the ROI 60 is enlarged and an M-mode image 65 of the ROI 60 (at a selection line 62 thereof) are displayed simultaneously.

The simultaneous display (dual mode display) of the B-mode image 64 and the M-mode image 65 may be performed in the same manner as the so-called B/M-mode display in a known ultrasound diagnostic apparatus.

Figure 5B:
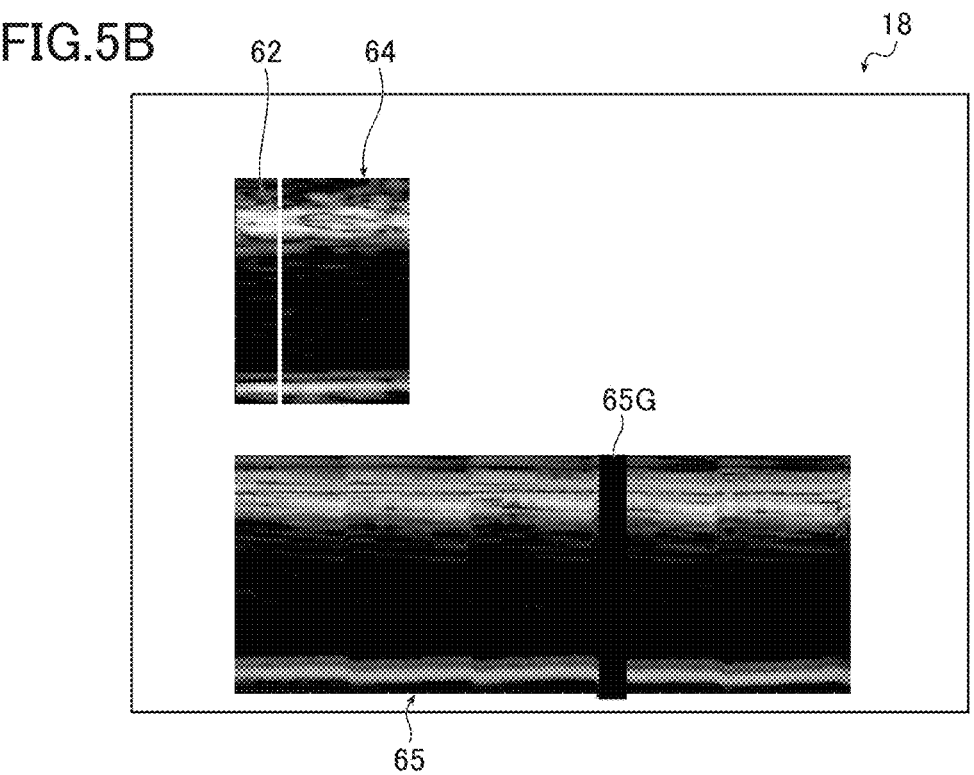

In FIG. 5B, the upper side is the B-mode image 64, and the lower side is the M-mode image 65.

In the B-mode image 64, the horizontal direction in the drawing is the azimuth direction (the direction along the array of the ultrasound transducers (in the case of the two-dimensional array, the longitudinal direction)), the vertical direction is the depth direction (the transmission/reception direction of ultrasonic waves), and the upper side is the side on which the depth is shallower (the probe 14 side).

A selection line 62 extending in the depth direction and used to select an M-mode image display position (a display line of the M-mode image) in the azimuth direction in the B-mode image is displayed in the B-mode image. The selection line 62 is movable in the azimuth direction (left-right direction) by the trackball.

In the M-mode image 65, the horizontal direction represents the time axis, the time flows from left to right, and the frame on the left side of a gap 65G. is a current frame (that is, the frame on the right side of the gap 65G is a past frame). Similarly to the B-mode image 64, the vertical direction is the depth direction and the upper side is the side on which the depth is shallower.

In FIG. 5B, the M-mode image 65 displayed on the display 18 is the M-mode image 65 of the position of the selection line 62 whose position is set in advance.

The M-mode image producing unit 58 produces not only an M-mode image of a predetermined position (a predetermined position set in advance or a selected position) in the azimuth direction or a selected position in the azimuth direction but also M-mode images over the entire region along the azimuth direction in the B-mode image 64.

The B-mode image (B-mode image data) of the ROI 60 produced by the B-mode image producing unit 56 and the M-mode image (M-mode image data) produced by the M-mode image producing unit 58 are both stored in the storage unit 36.

While the amount of an image stored in the storage unit 36 in terms of time is not particularly limited, a time length corresponding to two or more, preferably at least three heartbeats of common level is preferred. Accordingly, the storage unit 36 preferably stores the latest B-mode image and M-mode image each corresponding to three seconds or longer.

As described above, the selection line 62 is movable in the azimuth direction by the trackball.

The position of the selection line 62 and the M-mode image are linked with each other. Specifically, when the selection line 62 is moved in the left-right direction by the trackball, the display processing unit 52 displays an M-mode image of the position of the selected selection line 62 on the display 18.

Upon determining that an appropriate image (heartbeat) has been obtained, the operator presses the freeze button.

When the freeze button is pressed, the selection line 62 changes to a broken line and becomes immovable (becomes inactive).

Further, when the freeze button is pressed, the heartbeat detecting unit 46 detects heartbeats (performs automatic detection of heartbeats) for all the M-mode images stored in the storage unit 36. The detection result of heartbeats is sent to the display processing unit 52 and the storage unit 36 and, in the storage unit 36, are added to the corresponding M-mode images as information.

While a method of detecting heartbeats is not particularly limited, as an example, heartbeats may be detected by analyzing an M-mode image and using the moving velocity in the depth direction of a white line (bright line) extending in the horizontal direction (the time point at which the velocity starts to increase), the pulsation of the motion of the white line in the depth direction, and the like. Alternatively, an electrocardiograph (electrocardiogram) may be used to detect heartbeats.

Figure 6A:
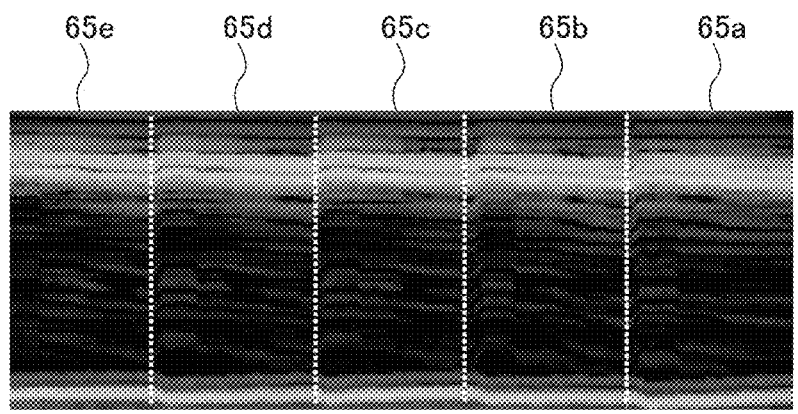
FIGS. 6A to 6C are conceptual diagrams each showing an example of image display in the ultrasound diagnostic apparatus shown in FIG. 1.

An example of a detection result of heartbeats in an M-mode image is shown in FIG. 6A.

In FIG. 6, boundaries of the heartbeats (each being the end of one heartbeat and, at the same time, the start of the next heartbeat) are indicated by broken lines. Thus, a complete heartbeat (fully-captured heartbeat) in the M-mode image is a heartbeat sandwiched between two broken lines. In FIG. 6, the image is rearranged so that the time at which the freeze button is pressed is located at the rightmost position (as the latest time) to make the function more understandable.

As an example, it is assumed that, as shown in FIG. 6A, a heartbeat 65a corresponding to the time of freeze, complete heartbeats 65b to 65d before the freeze, and an incomplete heartbeat 65e before the earliest complete heartbeat 65d are detected.

Figure 6B:
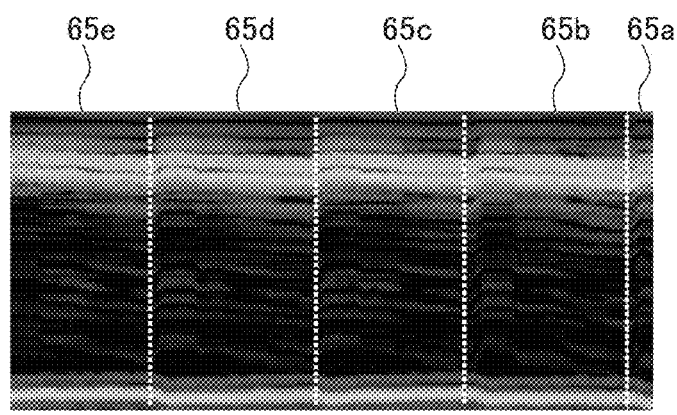

Upon receiving the detection result of heartbeats from the heartbeat detecting unit 46, the display processing unit 52 reads out necessary image data from the storage unit 36. Then, as shown in FIG. 6B, the display processing unit 52 produces an M-mode image for display so as to display the M-mode image after discarding (removing (deleting)) the heartbeat 65a corresponding to the freeze time (the time at which the freeze button is pressed). Specifically, the display processing unit 52 produces an M-mode image for display so as to display the M-mode image after discarding a newer region than the boundary of the latest heartbeat.

The discard of a heartbeat from the M-mode image is implemented only in the displayed image, and data is not deleted from the M-mode image stored in the storage unit 36.

Figure 6C:
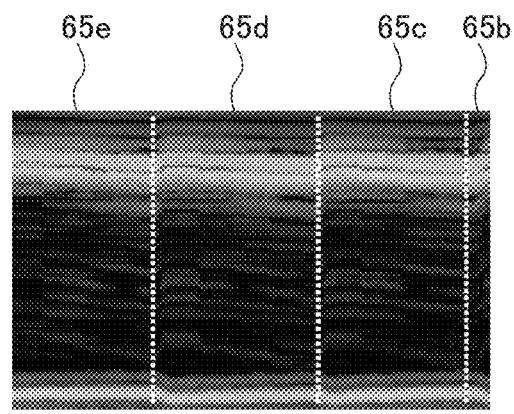

Alternatively, the display processing unit 52 produces an M-mode image for display so as to display the M-mode image after discarding also the heartbeat 65b which is the one immediately before the heartbeat 65a of the freeze time (hereinafter sometimes referred to as a heartbeat immediately before freeze) in addition to the heartbeat 65a corresponding to the freeze time, as shown in FIG. 6C.

Specifically, in this case, the display processing unit 52 produces an M-mode image for display so as to display the M-mode image after discarding a newer region than the boundary between the heartbeats 65b and 65c.

Whether the M-mode image is displayed after discarding only the heartbeat corresponding to the freeze time or discarding also the heartbeat immediately before freeze in addition, may be set in advance depending on the properties of the apparatus or the like.

Alternatively, the display of the M-mode image from which only the heartbeat corresponding to the freeze time is discarded may be defined as a first display mode whilst the display of the M-mode image from which the heartbeat corresponding to the freeze time and the heartbeat immediately before freeze are discarded may be defined as a second display mode, so that the tester such as a doctor who performs the ultrasound diagnosis can select the display mode. The display mode may be selected by a known means using a GUI, switching means, or the like.

In the illustrated examples in FIGS. 6B and 6C, taking into account the visibility when displayed in the M-mode image 65 on the display 18, a heartbeat is discarded so as to leave a slight margin (on a newer side) with respect to the boundary of the heartbeat indicated by a broken line, as described in detail below.

However, this invention is not limited thereto and the heartbeat to be discarded such as the heartbeat 65a may be wholly discarded for display.

In the case where a heartbeat is discarded so as to leave a margin to a heartbeat boundary, the amount of a remaining portion of the heartbeat may be determined by appropriately setting the amount that can clearly exhibit the fact that the heartbeat in question is discarded depending on the size of the displayed M-mode image in the time direction.

The image processing unit 52 having produced the M-mode image for display reads out data of a B-mode image from the storage unit 36 as needed, and as shown in FIG. 7A, the images are arranged in the longitudinal direction of the display 18 (generally a so-called H direction; hereinafter called "lateral direction") so that the B-mode image 64 and the M-mode image 65 are displayed on the left side and the right side in the drawing, respectively. Here, the azimuth direction of the B-mode image 64 and the time axis direction of the M-mode image 65 are identical.

The arrangement of the B-mode image 64 and the M-mode image 65 is not limited to the one shown in FIG. 7A. In the opposite way, the B-mode image 64 may be displayed on the right side in the drawing and the M-mode image may be displayed on the left side.

In the illustrated example, the display 18 can display the M-mode image corresponding only to slightly over one heartbeat in terms of size. Accordingly, as an example, the M-mode image 65 is displayed so that the latest heartbeat of non-discarded heartbeats is positioned in the center. In the present example, assuming that the image processing unit 52 produces the M-mode image for display in which the heartbeat 65*a* of the freeze time and the heartbeat 65*b* immediately before freeze are discarded, there is displayed the M-mode image 65 in which the heartbeat 65*c* before the heartbeat 65*b* immediately before freeze is positioned in the center.

Further, as shown in FIG. 7A, the display processing unit 52 displays the detection result of heartbeats by the heartbeat detecting unit 46 in the M-mode image 65 with triangular marks and straight lines (broken lines).

The B-mode image 64 at that time is a B-mode image at the start time of the heartbeat shown in the M-mode image 65 (at the position of the broken line on the left side in the drawing).

In the example shown in FIG. 7A, as a preferred embodiment, the B-mode image 64 and the M-mode image as arranged in the lateral direction are displayed, but this invention is not limited thereto.

Figure 8:
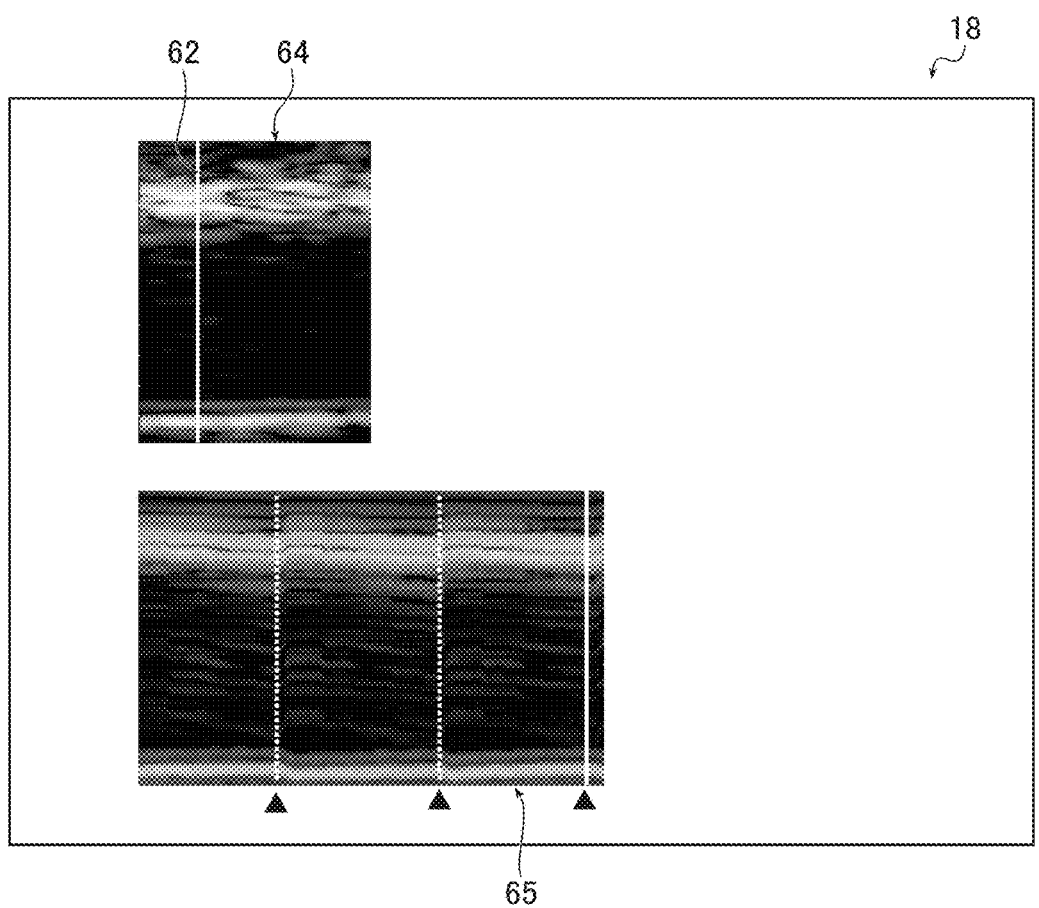
FIG. 8 is a conceptual diagram showing another example of image display in the ultrasound diagnostic apparatus shown in FIG. 1.

Specifically, as shown in FIG. 8 using the M-mode image of FIG. 6C in which the heartbeat of the freeze time and the heartbeat immediately before freeze are discarded, the B-mode image 64 and the M-mode image 65 may be displayed on the upper side and the lower side, respectively, on the display 18.

The image display with the lateral arrangement as shown in FIG. 7 is advantageous in that the B-mode image 64 and the M-mode image 65 can be displayed in large size.

Furthermore, in the image display with the lateral arrangement, when the displayed images are regulated to have the same magnification, the B-mode image 64 and the M-mode image 65 can be matched in terms of the position of a vascular wall or the like. Accordingly, when the operation such as setting of a boundary of a vascular wall in the B-mode image 64 to be described below is performed for instance, the process can be performed while referring to the M-mode image, advantageously. Conversely, when some kind of operation is performed in the M-mode image, the B-mode image can be referred to.

On the other hand, when the arrangement in the vertical direction as shown in FIG. 8 is employed, the M-mode image containing multiple heartbeats can be displayed.

As described in detail later, in order to perform the measurement of an elastic modulus of a vascular wall or the like, the analysis needs to be performed on an M-mode image of a complete heartbeat, i.e., an M-mode image having a heartbeat from the start through the end (the heartbeat is fully captured from the start through the end).

However, in the image display of the B/M mode, the M-mode image displayed at the time of freeze is to be an image at the time of freeze. The time of freeze hardly coincides with a boundary of a heartbeat and hence, in many cases, a heartbeat corresponding to the time of freeze tends to be an incomplete heartbeat which is not fully captured from the start to the end.

Specifically, in many cases, a heartbeat in the M-mode image at the time when freeze is performed is an unnecessary image (data) which is not used for image analysis.

Further, in order to perform favorable analysis, the use of an M-mode image which is less distorted due to hand movement of the tester is preferred.

Freeze of an ultrasound image is generally performed by pressing the freeze button as described above. During such operation, blurring due to hand movement of the tester easily occurs. Accordingly, even when a heartbeat is fully captured at the time of freeze, an M-mode image of the heartbeat immediately before freeze is likely to be an image which is adversely affected by blurring due to hand movement and thus not suitable for analysis.

On the other hand, in an ultrasound diagnostic apparatus, freeze is generally performed when the tester such as a doctor determines that an image favorable for analysis or diagnosis has been obtained.

Consequently, a heartbeat about one to three heartbeats before the heartbeat of the freeze time is highly possible to result in an M-mode image of a complete and favorable heartbeat which is not affected by blurring due to hand movement and is suitable for analysis for the measurement of a blood vessel elastic modulus or the like.

In the ultrasound diagnostic apparatus 10 of the invention, as described above, when freeze is performed in the image display of the B/M mode, the M-mode image 65 is displayed after discarding the heartbeat of the freeze time and possibly also the heartbeat immediately before freeze (after removing the same from the displayed image).

Therefore, according to the invention, the heartbeat of the freeze time which is not used for analysis and possibly also the heartbeat immediately before freeze which is likely to be inappropriate for analysis are not displayed, and only a heartbeat or heartbeats suitable for analysis can be displayed.

In particular, in the lateral arrangement of the B-mode image 64 and the M-mode image 65 as shown in FIG. 7, which is advantageous in that, for example, the images can be enlarged, the displayed M-mode image can have only one heartbeat or thereabout as described above. Accordingly, by discarding the heartbeat of the freeze time or the like, it becomes possible to discard an inappropriate heartbeat and display the M-mode image of a heartbeat suitable for analysis. Furthermore, in particular, an M-mode image having two or more heartbeats can be displayed in a recently-generalized wide screen (e.g., a landscape-oriented screen having an aspect ratio of 16:9 or more) even when employing the lateral arrangement, and hence, it becomes possible to more reliably display a heartbeat suitable for analysis after discarding an unnecessary heartbeat.

Further, by discarding an unnecessary portion of an M-mode image, the display space for the M-mode image 65 can be saved. Accordingly, the extra space after the discard can be effectively used for various purposes such as display of information. In particular, this effect is remarkable in the case of the vertical arrangement of the B-mode image 64 and the M-mode image 65 as shown in FIG. 8.

When the B-mode image 64 and the M-mode image 65 in which the heartbeat is displayed are displayed as described above, as shown in FIG. 7B, an "AW Det" button used for instructing the setting of a boundary of a vascular wall to be described below, an "Elasticity Ana" button used for instructing the start of analysis of a vascular wall elastic modulus, a "Ps" button and a "Pd" button used for inputting a blood pressure of the subject, and a "Quality Factor Threshold" button used for inputting a reliability threshold value are displayed in the touch panel 16a of the operating panel 16. Note that, at this time, the "Elasticity Ana" button is in the non-selectable state.

Further, when the B-mode image 64 and the M-mode image 65 in which the heartbeat is displayed are displayed, the selection line 62 in the B-mode image 64 changes to a solid line and becomes movable in the left-right direction with the use of the trackball. That is, the selection line 62 becomes active.

Whether or not the line is active may be distinguished by changing the line color instead of or in addition to the line type.

Under this condition, when the selection line 62 is moved in the left-right direction by the trackball, the display processing unit 52 reads out an M-mode image corresponding to the position of the selection line 62 from the storage unit 36, and displays the image along with the detection result of heartbeats on the display 18. Specifically, even after freeze, a display position (display line) of the M-mode image 65 in the B-mode image 64 can be selected from the entire region along the azimuth direction in the B-mode image 64 by moving the selection line 62 by the trackball.

Therefore, in the ultrasound diagnostic apparatus 10, the M-mode image 65 of an arbitrary position in the azimuth direction of the set ROI 60 is displayed, so that the M-mode image 65 and images corresponding to respective heartbeats in the M-mode image 65 can be observed and checked.

Also when the displayed M-mode image 65 (the display line 62 of the M-mode image 65 in the B-mode image 64) is changed in response to the movement of the selection line 62 through the trackball, the display processing unit 52 displays the M-mode image 65 after discarding the heartbeat of the freeze time and possibly also the heartbeat immediately before freeze.

Figure 9A:
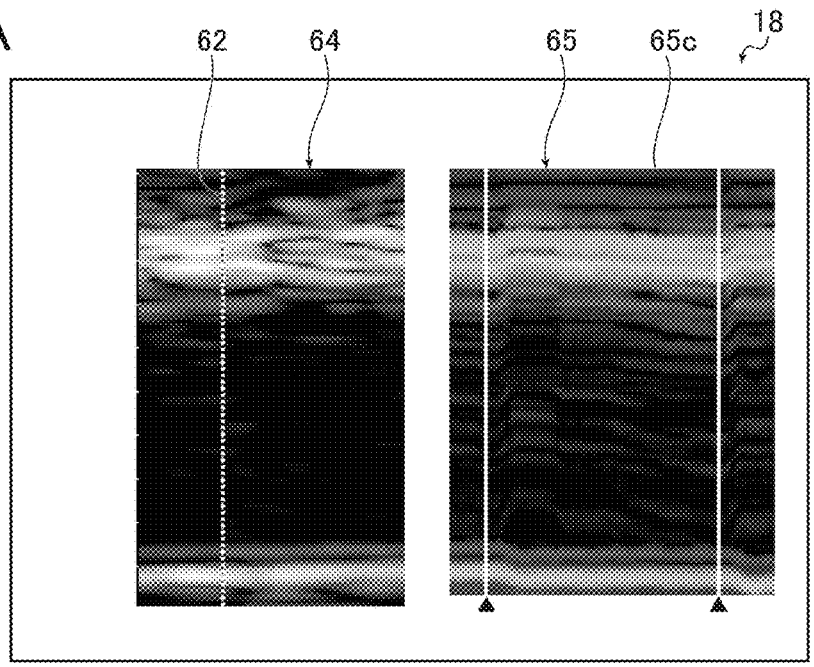
FIGS. 9A to 9C are conceptual diagrams each showing an example of image display in the ultrasound diagnostic apparatus shown in FIG. 1.

When the set button is pressed under the condition where the selection line 62 in the B-mode image 64 is movable, it is determined that the selection of the display position (display line) of the M-mode image has finished and, as shown in FIG. 9A, the selection line 62 in the B-mode image 64 changes to a broken line and the movement by the trackball becomes impossible.

Simultaneously, lines indicating the latest heartbeat both change to solid lines in the M-mode image 65.

When the lines indicating the latest heartbeat both change to solid lines in the M-mode image 65, the selection of a heartbeat with the use of the trackball becomes available.

Figure 9B:
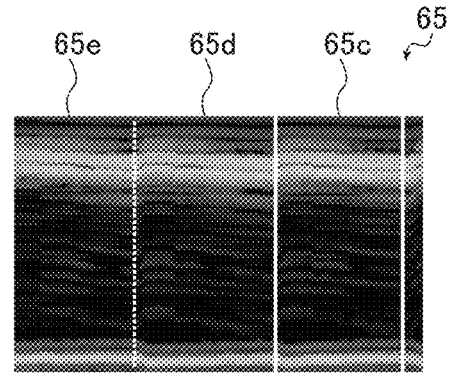
Figure 9C:
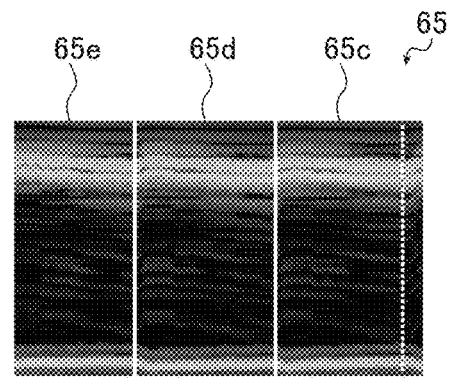

As an example, at the time when the set button is pressed, as shown by solid lines in FIGS. 9A and 9B, the latest heartbeat 65c of non-discarded heartbeats is displayed in the selected state. Under this condition, when the trackball is rotated left, as shown in FIG. 9C, a line corresponding to the end of the heartbeat 65c changes to a broken line and the second latest heartbeat 65d is selected as indicated by solid lines. In response, the display processing unit 52 scrolls the image to the right to display the heartbeat 65d in the center of the M-mode image 65.

When the trackball is rotated right, inversely a newer heartbeat is selected, and as shown in FIG. 9B, the heartbeat 65c is again selected. The display processing unit 52 scrolls the image to the left to display the heartbeat 65c in the center of the M-mode image 65.

In the case where the trackball is further rotated right under the condition where the heartbeat 65c is in the selected state, the display processing unit 52 need not scroll the image any further, or may read out necessary data from the storage unit 36 to display the discarded heartbeat 65b or heartbeat 65a in the M-mode image 65.

In response to the selection of a heartbeat, the display processing unit 52 reads out from the storage unit 36 the B-mode image of the start position of the selected heartbeat, that is, the B-mode image which is captured at the time (time phase) corresponding to the start position of the selected heartbeat, and changes the B-mode image 64 displayed on the display 18 to this image.

When the set button is pressed under the condition where the heartbeat selection is available, it is determined that the heartbeat selection has finished, the selected heartbeat is confirmed, and fine adjustment of the selected heartbeat becomes performable.

When the heartbeat in the M-mode image 65 displayed on the display 18 is selected and confirmed, the same heartbeat is selected in all the M-mode images stored in the storage unit 36 (that is, M-mode images over the entire region along the azimuth direction of the B-mode image 64).

As an example, assuming that the latest heartbeat 65c of displayed heartbeats is selected, when the set button is pressed, as shown in FIG. 10A, first, a line corresponding to the end of the heartbeat 65c changes to a broken line. Under this condition, the position (time) of a line corresponding to the start of the selected heartbeat 65c becomes movable in the left-right direction (time direction) with the use of the trackball as indicated by an arrow t, so that fine adjustment of the start position of the heartbeat can be performed.

After the start position of the heartbeat is adjusted by the trackball as needed, when the set button is pressed again, as shown in FIG. 10B, the line corresponding to the end of the selected heartbeat 65c changes to a solid line whilst the line corresponding to the start of the same heartbeat changes to a broken line. Under this condition, the position of the line corresponding to the end of the selected heartbeat 65c becomes movable in the left-right direction with the use of the trackball as indicated by an arrow t, so that fine adjustment of the end position of the heartbeat can be performed.

While the result of fine adjustment of the heartbeat may be reflected only in the M-mode image 65 subjected to the fine adjustment, the result is preferably reflected also in all the M-mode images stored in the storage unit 36.

In the case where the start position of the heartbeat is adjusted, the display processing unit 52 reads out the B-mode image of the adjusted heartbeat start position from the storage unit 36, and the B-mode image 64 displayed on the display 18 is changed to this image.

The results of the heartbeat selection and possible fine adjustment are supplied also to the tracking unit 42.

When the set button is pressed under the condition where the position corresponding to the end of the selected heartbeat is adjustable, the state of the selection line 62 in the B-mode image 64 shown in FIG. 7 mentioned above returns to be movable. That is, the state returns to the condition where the display line of the M-mode image 65 in the B-mode image 64 is selectable.

Thus, in the ultrasound diagnostic apparatus 10 of the illustrated example, the processes of "display line selection"→"heartbeat selection"→"heartbeat fine adjustment" can be repeatedly performed. In other words, the processes of "display line selection"→"heartbeat selection"→"heartbeat fine adjustment" can be performed in a looped manner.

Accordingly, it becomes possible to select the heartbeat optimal for analysis for the measurement of vascular wall elasticity to be described below from all the stored M-mode images in a further preferred manner.

Figure 11:
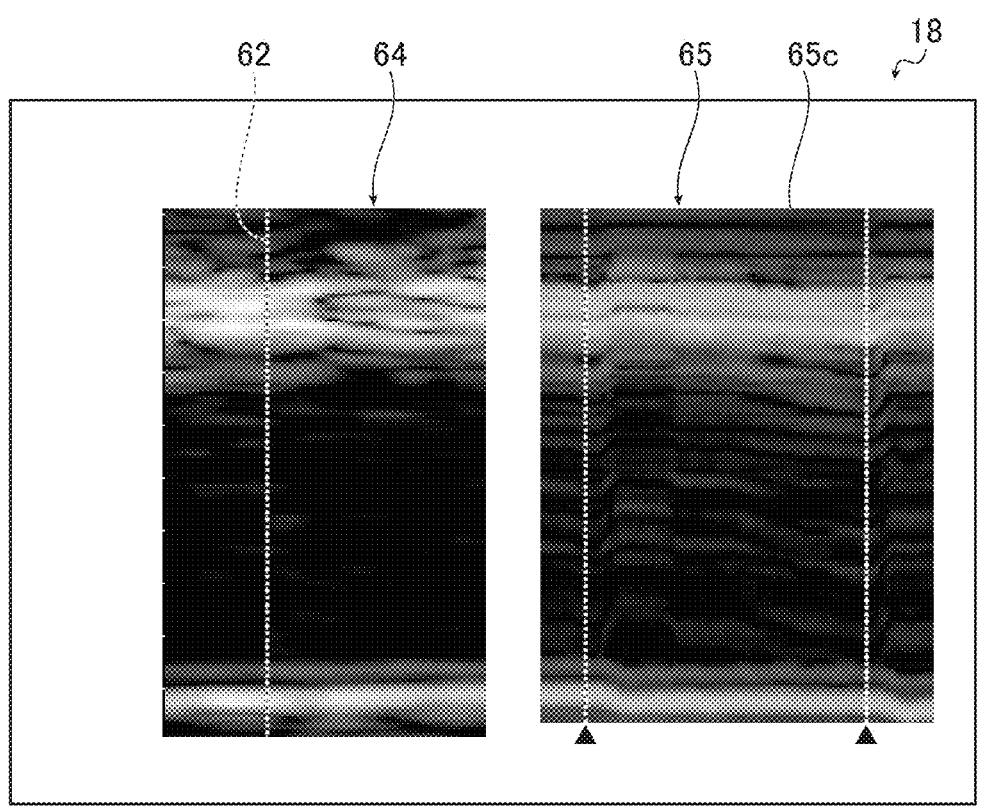
FIG. 11 is a conceptual diagram showing an example of image display in the ultrasound diagnostic apparatus shown in FIG. 1.

When not the set button but the "AW Det" button of the touch panel is pressed under the condition where the position corresponding to the end of the selected heartbeat is adjustable, as shown in FIG. 11, the selection line 62 in the B-mode image 64 and the lines representing the heartbeat in the M-mode image 65 all become broken lines and inoperable, and a vascular wall detection mode is established.

When the vascular wall detection mode is established, as shown in FIG. 12A, a line 68 corresponding to the adventitia-media boundary of the blood vessel anterior wall is displayed in the B-mode image 64.

The line 68 is movable parallel in the up-and-down direction (depth direction) by the trackball. As shown in FIG. 12B, when the line 68 is moved by the trackball to the position of the adventitia-media boundary of the blood vessel anterior wall, the set button is pressed.

When the set button is pressed, as shown in FIG. 12C, the line 68 corresponding to the adventitia-media boundary of the blood vessel anterior wall changes to a broken line in the B-mode image 64 and is thus confirmed, and a line 70 corresponding to the intima-lumen boundary of the blood vessel anterior wall is displayed.

Similarly, the line 70 is also movable in the up-and-down direction by the trackball, and when the line 70 is moved to the position of the intima-lumen boundary of the blood vessel anterior wall, the set button is pressed.

When the set button is pressed with the line 70 being movable, as shown in FIG. 12D, the line 70 corresponding to the intima-lumen boundary of the blood vessel anterior wall changes to a broken line in the B-mode image 64 and is thus confirmed, and a line 72 corresponding to the intima-lumen boundary of the blood vessel posterior wall is displayed. Similarly, when the line 72 is moved by the trackball to the position of the intima-lumen boundary of the blood vessel posterior wall, the set button is pressed.

Then, when the set button is pressed with the line 72 being movable, as shown in FIG. 12E, the line 72 corresponding to the intima-lumen boundary of the blood vessel posterior wall changes to a broken line in the B-mode image 64 and is thus confirmed, and a line 74 corresponding to the adventitia-media boundary of the blood vessel posterior wall is displayed. Similarly, when the line 74 is moved by the trackball to the position of the adventitia-media boundary of the blood vessel posterior wall, the set button is pressed.

Here, in the illustrated example, the B-mode image 64 and the M-mode image 65 are laterally arranged.

Hence, as described above, in comparison with the display in the vertical arrangement as shown in FIG. 8, both the B-mode image 64 and the M-mode image 65 can be displayed in large size. Furthermore, owing to the lateral arrangement, the B-mode image 64 and the M-mode image 65 can be adjusted in the display position so that positions of the vascular walls in the depth direction (up-and-down direction) in those images correspond to each other.

Thus, according to this example, with the use of the large B-mode image 64 and M-mode image 65, the boundaries of the vascular walls can be set in the B-mode image 64 while referring to the M-mode image 65, thereby enabling to easily and accurately set the boundaries.

Information on each boundary of the vascular walls is supplied to the boundary detecting unit 40.

When the set button is pressed with the line 74 being movable, the setting of the lines corresponding to all the boundaries finishes, and the boundary detecting unit 40 performs automatic detection of the intima-lumen boundary and the adventitia-media boundary of the posterior wall using the set line 72 for the intima-lumen boundary and the set line 74 for the adventitia-media boundary. The results of the automatic detection of the two boundaries are sent to the display processing unit 52 and the tracking unit 42, and as shown in FIG. 12F, the detection results are displayed.

A method of automatic detection of those boundaries is not particularly limited and several methods may be use. As an example, a method in which the B-mode image is analyzed and continuous high-intensity portions on the line 72 and the line 74 are traced to thereby detect the intima-lumen boundary and the adventitia-media boundary, is mentioned.

When the automatic detection of the intima-lumen boundary and the adventitia-media boundary of the blood vessel posterior wall by the boundary detecting unit 40 finishes, as shown in FIG. 12F, a cursor 78 is displayed in the B-mode image 64 (this cursor 78 is not displayed before the automatic detection of the blood vessel posterior wall finishes).

The cursor 78 is movable by the trackball. When the cursor 78 is moved toward either one of the lines indicative of the automatically-detected intima-lumen boundary and adventitia-media boundary and the set button is pressed, the line closer to the cursor 78 changes to a solid line. The line having changed to a solid line is correctable.

As an example, as shown in FIG. 12G, it is assumed that the line 74 indicative of the adventitia-media boundary is selected and changes to a solid line. When the cursor 78 is moved along the line 74 by the trackball and the set button is again pressed, the line 74 of the region traced by the cursor is again detected by the boundary detecting unit 40 and rewritten, and the result is sent to the tracking unit 42.

Figure 13A:
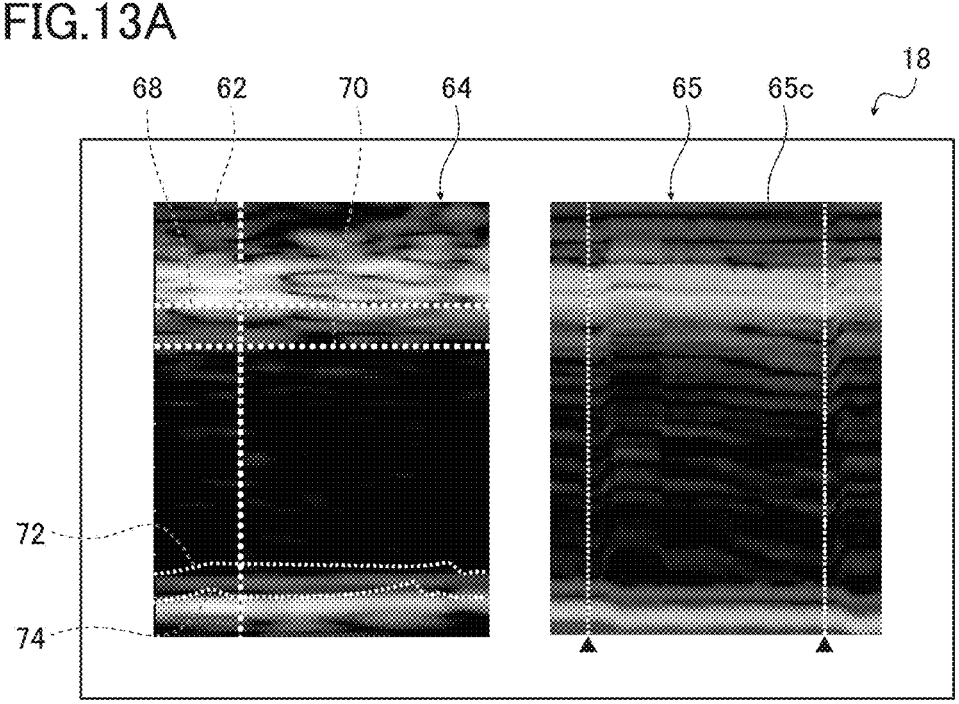
FIGS. 13A and 13B are conceptual diagrams each showing an example of image display in the ultrasound diagnostic apparatus shown in FIG. 1.
Figure 13B:
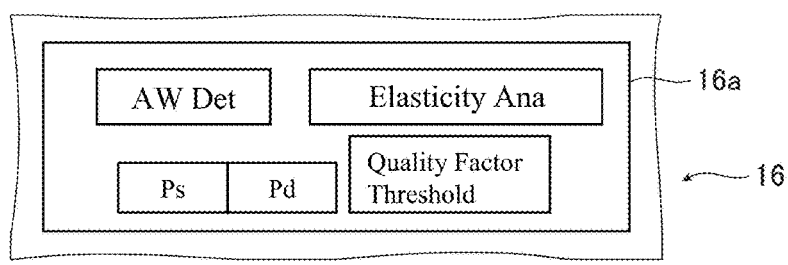

When the automatic detection of the intima-lumen boundary and the adventitia-media boundary of the posterior wall finishes and the blood vessel posterior wall is corrected as needed, as shown in FIG. 13A, all the lines become broken lines and as shown in FIG. 13B, the "Elasticity Ana" button of the touch panel 16a becomes selectable.

After the "Elasticity Ana" button becomes selectable, the systolic blood pressure of the subject is input using the "Ps" button whilst the end-diastolic blood pressure of the subject is input using the "Pd" button, and the reliability threshold value is input using the "Quality Factor Threshold" button. Those numerical values may be input by a known method.

The input of the blood pressure of the subject and the reliability threshold value is not limited to the input after the detection of the vascular wall boundaries finishes. Specifically, the input of the blood pressure of the subject and the reliability threshold value may be carried out at any timing as long as it is before the analysis described below starts (before depression of the "Elasticity Ana" button described below).

In the ultrasound diagnostic apparatus 10, subject information is normally acquired and input before a diagnosis is performed, and hence, when the subject information contains information on the blood pressure, this blood pressure information may be used.

When the blood pressure of the subject and the reliability threshold value are input and the "Elasticity Ana" button is pressed, analysis of the B-mode image starts and the elastic modulus of the vascular wall is calculated.

When the "Elasticity Ana" button is pressed, first, the tracking unit 42 performs tracking of motions of the blood vessel anterior wall (adventitia-media boundary and intima-lumen boundary) and the blood vessel posterior wall (intima-lumen boundary and adventitia-media boundary) in the selected heartbeat in the M-mode image 65. That is, the blood vessel anterior wall and posterior wall are tracked.

The tracking of the vascular wall in the M-mode image 65 is performed with the adventitia-media boundary of the blood vessel anterior wall, the intima-lumen boundary of the blood vessel anterior wall, the intima-lumen boundary of the blood vessel posterior wall, and the adventitia-media boundary of the blood vessel posterior wall as previously detected (set) in the B-mode image 64 being defined as positional starting points (starting points in the depth direction).

In the tracking of the vascular wall in the M-mode image 65, a temporal starting point (a starting point on the time axis of the M-mode image) is the time phase of the B-mode image 64, that is, the time at which the B-mode image 64 is captured. Specifically, in the illustrated example, the start position of the heartbeat which is selected and adjusted in position as needed is to be the temporal starting point for the tracking of the vascular wall.

In the ultrasound diagnostic apparatus 10, as a preferred embodiment, in addition to the detected (set) boundaries of the vascular walls, one or more measurement points may be set in the depth direction in the blood vessel posterior wall. In the case where one or more measurement points are thus set in the blood vessel posterior wall, the tracking of the vascular wall is performed at each measurement point.

The measurement point in the vascular wall may be set in advance, may be automatically set based on a specific algorithm, may be set by the operator of the ultrasound diagnostic apparatus 10 while viewing the image, or may be set through a combination of those methods.

A method of tracking the vascular wall in the M-mode image 65 is not particularly limited, and exemplary methods include a method which uses continuity of images (luminance) from the starting point of the tracking, a pattern matching method, a zero crossing method, a tissue Doppler method, and phase difference tracking, any of which may be used.

The results of tracking of the vascular walls in the M-mode image by the tracking unit 42 are supplied to the elastic modulus calculating unit 50 and the display processing unit 52.

The elastic modulus calculating unit 50 first produces a change waveform of the thickness of the vascular wall (intima-media) and a change waveform of the blood vessel diameter (inner diameter) based on the tracking results of the vascular wall. When one or more measurement points are set in the vascular wall as described above, a change waveform of the vascular wall is produced for each portion between measurement points.

The change waveform of the thickness of the vascular wall and the change waveform of the blood vessel diameter are sent to the display processing unit 52.

The elastic modulus calculating unit 50 calculates the strain of the blood vessel in the radial direction using Equation (1).

$$\varepsilon_i = \Delta h_i / h_{di} \quad (1)$$

In Equation (1), $\varepsilon_i$ denotes the strain of the blood vessel in the radial direction between measurement points, $\Delta h_i$ denotes the maximum value of a change in thickness of the vascular wall between the measurement points in systole in which the vascular wall is thinnest during one heartbeat, and $h_{di}$ denotes the thickness between the measurement points in end diastole in which the vascular wall is thickest.

Further, the elastic modulus calculating unit 50 calculates an elastic modulus $E_{\theta i}$ of the vascular wall in the circumferential direction by Equation (2) using the maximum value and the minimum value of the blood pressure input in advance.

$$E_{\theta 1} = 1/2 * [1 + (r_d/h_d)] * [\Delta p / (\Delta h_i / h_{di})] \quad (2)$$

Alternatively, an elastic modulus $E_{ri}$ of the vascular wall in the radial direction may be calculated by Equation (3).

$$E_{ri} = \Delta p / (\Delta h_i / h_{di}) \quad (3)$$

In Equations (2) and (3), $\Delta h_i$ and $h_{di}$ are the same as above, $\Delta p$ denotes a difference in blood pressure between systole and end diastole, $r_d$ denotes a radius of the vascular lumen in end diastole, and $h_d$ denotes the thickness of the vascular wall in end diastole.

After calculating the elastic modulus, the elastic modulus calculating unit 50 calculates the reliability of the elastic modulus.

A method of calculating the reliability of the elastic modulus is not particularly limited, and various known methods may be used. As an example, mentioned is a method in which waveforms of blood vessel diameter changes due to heartbeats of many people such as 1000 persons are produced; a model waveform of the blood vessel diameter change is produced based on those many waveforms; and the reliability of the calculated elastic modulus is calculated using a shift amount from the model waveform.

As described above, when a heartbeat is selected and confirmed in the M-mode image displayed on the display 18, the same heartbeat is selected in all the M-mode images stored in the storage unit 36.

Accordingly, the processes such as the tracking of the vascular wall, the production of the change waveforms of the thickness of the vascular wall and the blood vessel diameter, the calculation of the strain of the vascular wall, and the calculation of the elastic modulus of the vascular wall and the reliability of the elastic modulus, are performed for the selected heartbeat not only in the M-mode image 65 displayed on the display 18 but also in all the M-mode images stored in the storage unit 36. Specifically, the processes such as the calculation of the elastic modulus of the vascular wall in the selected heartbeat are performed for the entire region along the azimuth direction of the B-mode image 64 displayed on the display 18 using corresponding M-mode images.

Results of those are added to the M-mode images stored in the storage unit 36 as information.

After the calculation over the entire region along the azimuth direction finishes, the elastic modulus calculating unit 50 calculates the average value ($E_{\theta Ave}$) of the elastic modulus of the vascular wall, the average value ($Str_{Ave}$) of the strain of the vascular wall, and the average value ($QF_{Ave}$) of the reliability of the elastic modulus.

When the calculation finishes, the results are displayed on the display 18.

Figure 14:
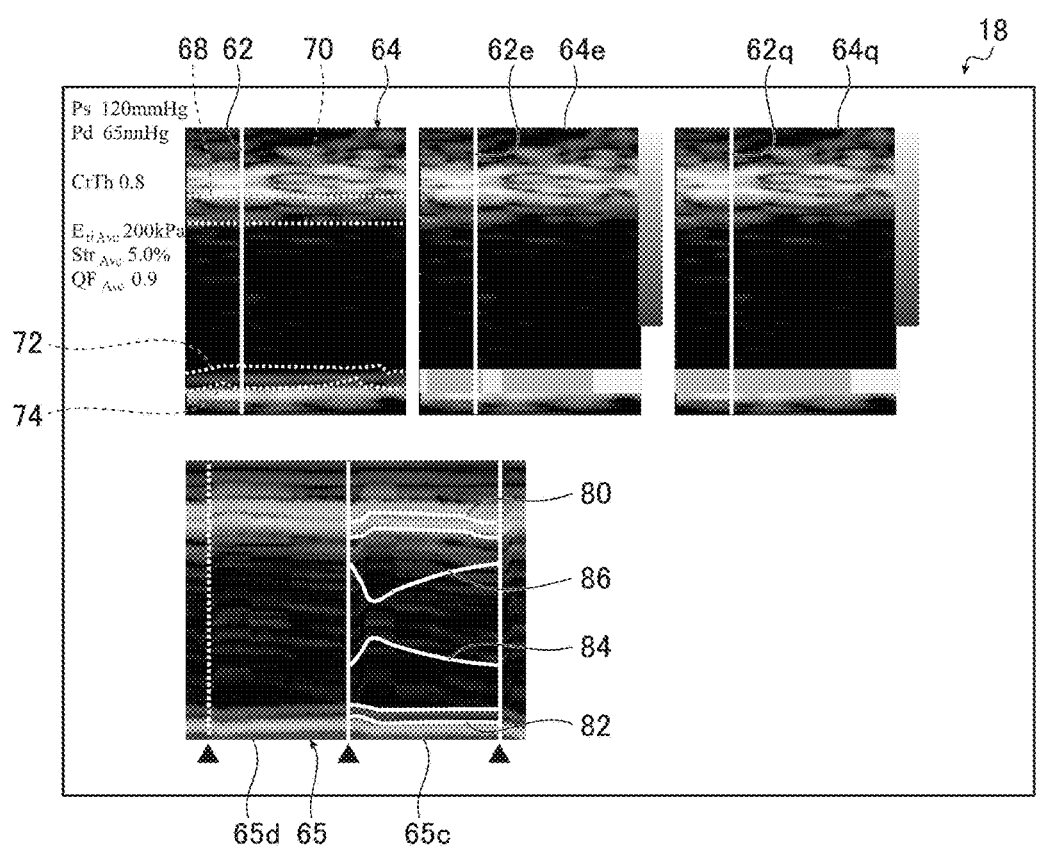
FIG. 14 is a conceptual diagram showing an example of image display in the ultrasound diagnostic apparatus shown in FIG. 1.

An example thereof is shown in FIG. 14. In this example, the display of the results is performed with the B-mode image 64 being displayed on the upper side and the M-mode image 65 on the lower side. Further, in the M-mode image, heartbeats having not been discarded are all displayed.

While the M-mode image 65 is arranged on the left side in the display frame of the display 18 in the example shown in FIG. 14, the invention is not limited thereto. Specifically, in the invention, the M-mode image 65 may be displayed so that the M-mode image 65 is arranged on the right side in the display frame of the display 18 and the latest frame is positioned on the right side of the display frame. Alternatively, it may be positioned in the center of the display frame of the M-mode image 65.

In the illustrated example, the original B-mode image 64 used for analysis is displayed on the left side in the drawing, and the elastic modulus of the blood vessel posterior wall shown in this B-mode image 64 is displayed in a B-mode image 64*e* on the right side of the original B-mode image 64 in the drawing. Further, on the right side in the drawing of the B-mode image 64*e* which displays the elastic modulus of the blood vessel posterior wall, the calculated reliability of the elastic modulus of the vascular wall is displayed in a B-mode image 64*q* in a similar manner.

On the left side in the drawing of the B-mode image 64, the average value ($E_{\theta Ave}$) of the elastic modulus of the vascular wall, the average value ($Str_{Ave}$) of the strain of the vascular wall, and the average value ($QF_{Ave}$) of the reliability of the elastic modulus are displayed.

The elastic modulus of the vascular wall is displayed in a strip shape in the B-mode image 64*e* so as to overlap the blood vessel posterior wall automatically detected (and corrected as needed) in the B-mode image 64. On an upper right side of the B-mode image 64*e*, an index of the elastic modulus is displayed. In the illustrated example, the higher the image density is, the higher the elastic modulus is.

Specifically, in the B-mode image 64*e*, the density of the strip overlapping the blood vessel posterior wall represents the elastic modulus of the vascular wall at that position of the blood vessel.

Similarly, the reliability of the elastic modulus is displayed in a strip shape in the B-mode image 64*q* so as to overlap the blood vessel posterior wall automatically detected in the B-mode image 64. On an upper right side of the B-mode image 64*q*, an index of the reliability of the elastic modulus is displayed. In the illustrated example, the higher the image density is, the higher the reliability of the elastic modulus is.

Specifically, in the B-mode image 64*q*, the density of the strip overlapping the blood vessel posterior wall represents the reliability of the elastic modulus of the vascular wall at that position of the blood vessel.

The magnitude of the elastic modulus or the reliability of the elastic modulus may be expressed by changing the color of the image instead of or in addition to the density of the image.

In the display of the results shown in FIG. 14, the result at the position in the azimuth direction where the reliability is lower than the threshold value input in advance is automatically omitted.

At the position where the result is omitted, as indicated in the right corner portion of the result display of the elastic modulus in the B-mode image 64*e* and the right corner portion of the result display of the reliability in the B-mode image 64*q*, the display of the strip becomes pale.

In the M-mode image 65 on the lower side, a tracking result 80 of the blood vessel anterior wall and a tracking result 82 of the blood vessel posterior wall as well as a change waveform 84 of the blood vessel diameter and a change waveform 86 of the thickness of the vascular wall in the M-mode image, are displayed in the selected heartbeat.

As described above, when one or more measurement points are set in the vascular wall in the depth direction, the change waveform of the blood vessel thickness may be output for each portion between measurement points.

When the measurement result of the elastic modulus of the vascular wall and the like are displayed on the display 18, the selection line 62 in the B-mode image 64 changes to a solid line and becomes movable in the azimuth direction by the trackball.

When the selection line 62 is moved in the B-mode image 64, the display processing unit 52 reads out an M-mode image corresponding to the position of the selection line 62 from the storage unit 36 and displays the M-mode image on the display 18. Specifically, when the selection line 62 is moved by the trackball, the M-mode image 65 is changed to an M-mode image of the position of the selection line 62, and the tracking result 80 of the blood vessel anterior wall and the tracking result 82 of the blood vessel posterior wall as well as the change waveform 84 of the blood vessel diameter and the change waveform 86 of the thickness of the vascular wall in the M-mode image are changed to data at the position of the selection line 62 of the B-mode image 64.

Accordingly, it is possible to select a display line used for displaying the M-mode image 65 and the analysis result in the entire region along the azimuth direction of the B-mode image.

In synchronization with the movement of the selection line 62 in the B-mode image 64, a selection line 62*e* in the B-mode image 64*e* and a selection line 62*q* in the B-mode image 64*q* are also moved.

After the set button is pressed, when the selection line 62*e* and the selection line 62*q* are moved by the trackball to select an arbitrary region along the azimuth direction in the B-mode image 64*e* and the B-mode image 64*q*, and thereafter, the set button is pressed again, the selected region is treated similarly to the above-mentioned region where the reliability is lower than the threshold value, so that data is deleted.

Specifically, when the tester views the result and finds a location where the waveform or the like seems strange, the corresponding data can be deleted, thereby making it possible to perform more accurate analysis.

In this operation of deleting data, the previous condition may be restored by depressing a Delete button or the like.

While the ultrasound diagnostic apparatus of the invention has been described above in detail, the invention is by no means limited to the above examples, and various modifications and improvements may be made without departing from the scope and spirit of the invention.

What is claimed is:

1. An ultrasound diagnostic apparatus comprising:
an ultrasound probe which has ultrasound transducers, wherein the ultrasound transducers are configured to transmit ultrasonic waves, receive an ultrasonic echo reflected by a subject, and output a reception signal according to the received ultrasonic echo;
a display;
an operating panel; and
a processor, wherein:
the processor is configured to produce a first B-mode image and a first M-mode image from the reception signal output from the ultrasound transducers,
the processor is configured to display on the display the first B-mode image and the first M-mode image,
the processor is configured to pause an image depending on an input instruction to the operation panel,
the processor is configured to detect a plurality of heartbeats in the first M-mode image,
the processor is configured to perform tracking of motion of a vascular wall in the first M-mode image which is displayed on the display, and
the processor is configured to calculate an elastic modulus of the vascular wall based on tracking results of the vascular wall,
wherein, in a case that image pausing is instructed with the first B-mode image and the first M-mode image being displayed on the display, the processor is further configured:
to cause a non-transitory storage device to store a second M-mode image comprising a portion of the first M-mode image representing an interval from the point of instructing the image pausing to a predetermined period before the instruction of image pausing;

to set boundaries of the plurality of detected heartbeats in the second M-mode image, wherein each pair of boundaries delimits a heartbeat region;

to discard from the delimited heartbeat regions in the second M-mode image both an entire first heartbeat region representing a heartbeat which occurred at the point in time when the image pausing was instructed and at least a part of a second heartbeat region adjacent to the first heartbeat region representing a heartbeat which occurred immediately before the point in time when the image pausing was instructed, on a side adjacent to the first heartbeat region, the entire first heartbeat region and the at least a part of the second heartbeat region being heartbeat regions possibly blurred by pressing a freeze button, to form a third M-mode image having at least one complete heartbeat from a start of the at least one heartbeat through an end of the at least one heartbeat;

to update the display by displaying the third M-mode image;

to select one of the at least one complete heartbeat in the displayed third M-mode image; and to update the display by displaying both a second B-mode image which is captured at a time coincident with a start position of the selected complete heartbeat and a fourth M-mode image comprising the selected complete heartbeat side by side.

2. The ultrasound diagnostic apparatus according to claim 1, wherein in the case that the image pausing is instructed, the processor is further configured to display the first M-mode image and the first B-mode image side by side on the display.

3. The ultrasound diagnostic apparatus according to claim 1,
wherein the processor is further configured to set a boundary of the vascular wall in the second B-mode image displayed on the display after image pausing is instructed, in the case that image pausing is instructed, in the case that image pausing is instructed.

4. The ultrasound diagnostic apparatus according to claim 1,
wherein the processor is further configured to set a region of interest in the first B-mode image at the point in time when the image pausing is instructed, and displaying the first region of interest on the display.

5. The ultrasound diagnostic apparatus according to claim 4, wherein a frame rate of ultrasonic waves transmitted by the ultrasound transducers after the region of interest is set is higher than a frame rate of ultrasonic waves transmitted by the ultrasound transducers before the region of interest is set.

6. The ultrasound diagnostic apparatus according to claim 1, wherein the processor is configured to set boundaries of the vascular walls in the second B-mode image with respect to the fourth M-mode image, and to perform tracking of motion of the vascular walls in the selected complete heartbeat in the fourth M-mode image, using information on the set boundaries of the vascular walls.

7. The ultrasound diagnostic apparatus according to claim 1, wherein the processor is configured to set automatically the boundaries of the heartbeats in the second M-mode image, each boundary being an end of one heartbeat and a start of a next heartbeat for the entire second M-mode image, thereby performing automatic setting of the heartbeat regions.

8. The ultrasound diagnostic apparatus according to claim 7, wherein the processor is configured to perform automatic setting of the heartbeat regions by analyzing the second M-mode image and using a moving velocity in a depth direction of a bright line extending in a horizontal direction in the second M-mode image, or pulsation of motion of the bright line in the depth direction.

9. The ultrasound diagnostic apparatus according to claim 8, wherein the processor is configured to perform automatic setting of the heartbeat regions using a time point at which the moving velocity starts to increase.

10. The ultrasound diagnostic apparatus according to claim 1, wherein the fourth M-mode image is an image of a remainder region which was not discarded in the second heartbeat region and a region of the selected complete heartbeat adjacent to the second heartbeat region.

11. The ultrasound diagnostic apparatus according to claim 1, wherein the second B-mode image and the fourth M-mode image are displayed side by side in a horizontal direction or a vertical direction on the display.

* * * * *